United States Patent
Fernstrom et al.

(10) Patent No.: US 10,900,943 B2
(45) Date of Patent: *Jan. 26, 2021

(54) METHOD, APPARATUS AND SYSTEM FOR FOOD INTAKE AND PHYSICAL ACTIVITY ASSESSMENT

(71) Applicant: University of Pittsburgh—Of the Commonwealth System of Higher Education, Pittsburgh, PA (US)

(72) Inventors: John Fernstrom, Pittsburgh, PA (US); Madelyn Fernstrom, Pittsburgh, PA (US); Wenyan Jia, Wexford, PA (US); Robert Sclabassi, Gibsonia, PA (US); Mingui Sun, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 146 days.

This patent is subject to a terminal disclaimer.

(21) Appl. No.: 15/994,003

(22) Filed: May 31, 2018

(65) Prior Publication Data

US 2018/0348187 A1    Dec. 6, 2018

Related U.S. Application Data

(63) Continuation of application No. 13/676,468, filed on Nov. 14, 2012, now Pat. No. 10,006,896.
(Continued)

(51) Int. Cl.
*G01N 33/02* (2006.01)
*A61B 5/11* (2006.01)
(Continued)

(52) U.S. Cl.
CPC ........... *G01N 33/02* (2013.01); *A61B 5/0022* (2013.01); *A61B 5/0024* (2013.01);
(Continued)

(58) Field of Classification Search
None
See application file for complete search history.

(56) References Cited

U.S. PATENT DOCUMENTS 3,069,654 A    12/1962  Hough
4,664,129 A *   5/1987  Helzel ................. A61B 5/1107
                                                    600/534
(Continued)

FOREIGN PATENT DOCUMENTS

WO    2012115297 A1    8/2012

OTHER PUBLICATIONS

Sclasbassi et al., "An Acoustic Aneurysm-Detector", Medical Instrumentation, 1987, pp. 317-322, vol. 21:6.
(Continued)

*Primary Examiner* — Carl H Layno
*Assistant Examiner* — Manolis Pahakis
(74) *Attorney, Agent, or Firm* — The Webb Law Firm

(57) ABSTRACT

Electronic systems, devices and methods are provided to accurately record and analyze food intake and physical activity in a subject. A device is provided to be placed on a subject which records video using at least two video cameras positioned to record stereoscopic image pair, as well as other physiological and/or environmental data including, for example, oxygen saturation, heart rate, and environmental factors such as physical location, temperature, and humidity. Video data is analyzed along with other data obtained by the device to determine food consumption and/or physical activity of the subject, much of which is accomplished by automated computer-implemented processes.

20 Claims, 8 Drawing Sheets

Related U.S. Application Data

(60) Provisional application No. 61/559,370, filed on Nov. 14, 2011.

(51) Int. Cl.

| | | |
|---|---|---|
| *G01N 21/00* | (2006.01) | |
| *A61B 5/04* | (2006.01) | |
| *A61B 7/00* | (2006.01) | |
| *A61B 5/00* | (2006.01) | |
| *G16H 40/67* | (2018.01) | |
| *G16H 20/30* | (2018.01) | |
| *G16H 20/60* | (2018.01) | |
| *A61B 5/1455* | (2006.01) | |
| *A61B 5/0205* | (2006.01) | |
| *A61B 5/01* | (2006.01) | |

(52) U.S. Cl.
CPC .............. *A61B 5/0077* (2013.01); *A61B 5/04* (2013.01); *A61B 5/1112* (2013.01); *A61B 5/1118* (2013.01); *A61B 5/6802* (2013.01); *A61B 5/6805* (2013.01); *A61B 5/6816* (2013.01); *A61B 7/00* (2013.01); *G01N 21/00* (2013.01); *G16H 20/30* (2018.01); *G16H 20/60* (2018.01); *G16H 40/67* (2018.01); *A61B 5/01* (2013.01); *A61B 5/02055* (2013.01); *A61B 5/14551* (2013.01); *Y02A 90/10* (2018.01)

(56) References Cited

U.S. PATENT DOCUMENTS

| | | | |
|---|---|---|---|
| 4,823,808 A | 4/1989 | Clegg et al. | |
| 4,965,533 A | 10/1990 | Gilmore | |
| 4,965,553 A * | 10/1990 | DelBiondo, II | G08B 21/0453 340/573.1 |
| 5,755,744 A | 5/1998 | Shaw et al. | |
| 6,364,849 B1 | 4/2002 | Wilcox | |
| 6,445,942 B1 | 9/2002 | Berthon-Jones et al. | |
| 6,508,762 B2 | 1/2003 | Karnieli | |
| 6,527,711 B1 | 3/2003 | Stivoric et al. | |
| 6,553,386 B1 | 4/2003 | Alabaster | |
| 6,735,477 B2 | 5/2004 | Levine | |
| 6,922,184 B2 | 7/2005 | Lawrence et al. | |
| 6,932,766 B2 | 8/2005 | Bergh et al. | |
| 9,198,621 B2 * | 12/2015 | Fernstrom | A61B 5/1123 |
| 9,424,495 B1 | 8/2016 | Trevino | |
| 2002/0022774 A1 * | 2/2002 | Karnieli | G06F 19/324 600/300 |
| 2002/0109600 A1 * | 8/2002 | Mault | A61B 5/1112 340/573.1 |
| 2003/0055414 A1 | 3/2003 | Altshuler et al. | |
| 2003/0063775 A1 | 4/2003 | Rafii et al. | |
| 2003/0097254 A1 | 5/2003 | Holzrichter et al. | |
| 2003/0125623 A1 | 7/2003 | Kelly et al. | |
| 2003/0135097 A1 | 7/2003 | Wiederhold et al. | |
| 2003/0187369 A1 * | 10/2003 | Lewis | A61B 5/1076 600/587 |
| 2004/0136569 A1 | 7/2004 | Daley et al. | |
| 2004/0221847 A1 * | 11/2004 | Berthon-Jones | A61M 16/026 128/204.18 |
| 2004/0242976 A1 | 12/2004 | Abreu | |
| 2005/0075798 A1 | 4/2005 | Edwards et al. | |
| 2005/0107654 A1 * | 5/2005 | Riehl | A61N 2/006 600/9 |
| 2006/0009702 A1 | 1/2006 | Iwaki et al. | |
| 2006/0064037 A1 | 3/2006 | Shalon et al. | |
| 2006/0200115 A1 * | 9/2006 | Ferren | A61B 18/203 606/9 |
| 2006/0200116 A1 | 9/2006 | Ferren et al. | |
| 2007/0002039 A1 | 1/2007 | Pendleton et al. | |
| 2007/0016098 A1 | 1/2007 | Kim et al. | |
| 2007/0060336 A1 | 3/2007 | Marks et al. | |
| 2007/0073361 A1 * | 3/2007 | Goren | A61B 5/04 607/62 |
| 2007/0106127 A1 | 5/2007 | Alman | |
| 2007/0282318 A1 | 12/2007 | Spooner et al. | |
| 2008/0071180 A1 | 3/2008 | Borgos | |
| 2008/0146890 A1 | 6/2008 | LeBoeuf et al. | |
| 2008/0267444 A1 | 10/2008 | Simons-Nikolova et al. | |
| 2009/0012433 A1 | 1/2009 | Fernstrom et al. | |
| 2009/0030346 A1 | 1/2009 | Kojima et al. | |
| 2009/0080706 A1 | 3/2009 | Tao et al. | |
| 2009/0190798 A1 | 7/2009 | Lee et al. | |
| 2009/0238460 A1 | 9/2009 | Funayama et al. | |
| 2009/0268031 A1 | 10/2009 | Honma et al. | |
| 2010/0105306 A1 | 4/2010 | Daley et al. | |
| 2010/0111383 A1 | 5/2010 | Boushey et al. | |
| 2010/0173269 A1 | 7/2010 | Puri et al. | |
| 2010/0232647 A1 | 9/2010 | Fujieda et al. | |
| 2011/0182477 A1 | 7/2011 | Tamrakar et al. | |
| 2011/0295083 A1 | 12/2011 | Doelling et al. | |
| 2013/0099009 A1 * | 4/2013 | Filson | F24F 11/50 236/1 C |
| 2013/0335418 A1 | 12/2013 | Kim et al. | |
| 2014/0273858 A1 | 9/2014 | Panther et al. | |
| 2016/0073886 A1 | 3/2016 | Connor | |
| 2016/0317060 A1 | 11/2016 | Connor | |
| 2017/0358241 A1 * | 12/2017 | Wexler | G06K 9/00362 |
| 2019/0340440 A1 * | 11/2019 | Atwater | A01K 61/80 |
| 2020/0005455 A1 * | 1/2020 | Alshurafa | G06K 9/00671 |

OTHER PUBLICATIONS

Sclabassi et al., "EEG source localization: A neural network approach", Neurological Research, 2001, pp. 457-464, vol. 23.

Sclabassi et al., "Laboratory Computers in Neurophysiology", Proceedings of the IEEE, 1973, pp. 1602-1614, vol. 61:11.

Sclabassi et al., "The Multi-Media Medical Monitoring, Diagnosis, and Consultation Project", Proceedings of the Twenty-Fourth Annual Hawaii International Conference, 1991, pp. 717-728, vol. 3.

Seale et al., "Comparison of energy expenditure measurements by diet records, energy intake balance, doubly labeled water and room calorimetry", European Journal of Clinical Nutrition, 1997, pp. 856-863, vol. 51.

Sekhar et al., "Intra-aneurysmal pressure measurements in experimental saccular aneurysms in dogs", Stroke, 1988, pp. 352-356, vol. 19.

Sekihara et al., "Application of an MEG Eigenspace Beamformer to Reconstructing Spatio-Temporal Activities of Neural Sources", Human Brain Mapping, 2002, pp. 199-215, vol. 15.

Sekihara et al., "Estimating Neural Sources From Each Time-Frequency Component of Magnetoencephalographic Data", IEEE, 1998, pp. 69-72.

Sekihara et al., "Estimating Neural Sources from Each Time-Frequency Component of Magnetoencephalographic Data", IEEE Transactions on Biomedical Engineering, 2000, pp. 642-653, vol. 47:5.

Sekihara et al., "Noise Covariance Incorporated MEG-MUSIC Algorithm: A Method for Multiple-Dipole Estimation Tolerant of the Influence of Background Brain Activity", IEEE Transactions on Biomedical Engineering, 1997, pp. 839-847, vol. 44:9.

Sekihara et al., "Reconstructing Spatio-Temoral Activities of Neural Sources Using an MEG Vector Beamformer Technique", IEEE Transactions of Biomedical Engineering, 2001, pp. 760-771, vol. 48:7.

Sekihara et al., "Time-Frequency MEG-MUSIC Algorithm", IEEE Transactions on Medical Imaging, 1999, pp. 92-97, vol. 18:1.

Senuzun et al., "Effects of home-based cardiac exercise program on the exercise tolerance, serum lipid values and self-efficacy of coronary patients", European Journal of Cardiovascular Prevention & Rehabilitation, 2006, pp. 640-645.

Sevick et al., "A PDA-based dietary self-monitoring intervention to reduce sodium intake in an in-center hemodialysis patient", Patient Preferences and Adherence, 2008, pp. 177-184, vol. 2.

Sevick et al., "Design, feasibility, and acceptability of an intervention using personal digital assistant-based self-monitoring in managing type 2 diabetes", Contemp Clin Trials, 2008, pp. 396-409, vol. 29:3.

(56) References Cited

OTHER PUBLICATIONS

Sevick et al., "Factors associated with probability of personal digital assistant-based dietary self-monitoring in those with type 2 diabetes", J Behav Med, 2010, pp. 315-325, vol. 33.

Sierra et al., "Comparison of Respiratory Rate Estimation Based on Tracheal Sounds Versus a Capnograph", Proceedings of the 2005 IEEE Engineering in Medicine and Biology 27th Annual Conference, 2005, pp. 6145-6148.

Simon et al., "Multimedia MedNet: A Medical Collaboration and Consultation System", IEEE, 1995, pp. 65-73.

Song et al., "Body Image and Quality of Life in Post Massive Weight Loss Body Contouring Patients", Obesity, 2006, pp. 1626-1636, vol. 14.

Sonmez et al., "A Hierarchical Decision Module Based on Multiple Neural Networks", IEEE, 1997, pp. 238-241.

Sonmez et al., "Extension of a Training Set for Artificial Neural Networks and Its Application to Brain Source Localization", IEEE, 1996, pp. 635-640.

Sovijarvi et al., "A new versatile PC-based lung sound analyzer with automatic crackle analysis (HeLSA); repeatability of spectral parameters and sound amplitude in healthy subjects", Technology and Health Care, 1998, pp. 11-22, vol. 6.

Spong et al., "Controlled Symmetries and Passive Walking", IFAC W.C., 2002, pp. 1025-1031.

Stein et al., "The Epidemic of Obesity", J Clin Endocrinol Metab, 2004, pp. 2522-2525, vol. 89.

Subar et al., "Assessment of the Accuracy of Portion Size Reports Using Computer-Based Food Photographs Aids in the Development of an Automated Self-Administered 24-Hour Recall", J Am Diet Assoc., 2010, pp. 55-64, vol. 110:1.

Sun et al., "A Human-Centric Smart System Assisting People in Healthy Diet and Active Living", Proc. Int. Symp. Digital Life Technologies: Human-Centric Smart Living Technology, pp. 1-4.

Sun et al., "A Multimedia System for Remote Neurosurgical Monitoring", IEEE, 2004, pp. 379-383.

Sun et al., "A Volume Conduction Antenna for Implantable Devices", Proceedings of the 25th Annual International Conference of the IEEE EMBS, 2003, pp. 3356-3359.

Sun et al., "A Wearable Electronic System for Objective Dietary Assessment", J Am Diet Assoc., 2010, pp. 1-6, vol. 110:1.

Sun et al., "Assessment of Food Intake and Physical Activity: A Computational Approach", Handbook of Pattern Recognition and Computer Vision, 2009, pp. 1-20, vol. 4.

Sun et al., "Assessment of Object-Based Video Compression for Epilepsy Monitoring", Proceedings of the Second Joint EMBS/BMES Conference, 2002, pp. 1045-1046.

Sun et al., "Decomposition of biomedical signals for enhancement of their time-frequency distributions", Journal of the Franklin Institute, 2000, pp. 453-467, vol. 337.

Sun et al., "Determination of Food Portion Size by Image Processing", 30th Annual International IEEE EMBS Conference, 2008, pp. 871-874.

Sun et al., "Extraction and Analysis of Early Ictal Activity in Subdural Electroencephalogram", Annals of Biomedical Engineering, 2001, pp. 878-886, vol. 29.

Sun et al., "Passing Data and Supplying Power to Neural Implants", IEEE Engineering in Medicine and Biology Magazine, 2006, pp. 39-46.

Sun et al., "Platform Technologies for Minimally Invasive Physiological Monitoring", Proceedings of the 25th Army Science Conference, 2006.

Sun et al., "Precise Determination of Starting Time of Epileptic Seizures Using Subdural EEG and Wavelet Transforms", IEEE, 1998, pp. 257-260.

Sun et al., "Recording and processing aneurysmal vibration signals in dogs", J. Biomed. Eng., 1988, pp. 336-342, vol. 10.

Sun et al., "Sample Domain Integration of Medical Data for Multimedia Diagnosis", IEEE, 2002, pp. 363-366.

Sun et al., "Soft Computation of Numerical Solutions to Differential Equations in EEG Analysis", Intelligent Multimedia Processing with Soft Computing, 2005, pp. 431-451.

Sun et al., "Solving Partial Differential Equations in Real-Time Using Artificial Neural Network Signal Processing as an Alternative to Finite Element Analysis", IEEE Int. Conf. Neural Networks & Signal Processing, 2003, pp. 381-384.

Sun et al., "Time-Frequency Distributions of Subdural EEG at Epileptic Seizure Onset", IEEE, 1998, pp. 73-76.

Sun et al., "Wavelet Feature Extraction from Neurophysiological Signals", 1998, pp. 305-321, John Wiley & Sons Retrieved.

Sural et al., "Segmentation and Histogram Generation Using the HSV Color Space for Image Retrieval", IEEE, 2002, pp. 589-592.

Tharion et al., "Adequacy of Garrison Feeding for Special Forces Soldiers during Training", Military Medicine, 2004, pp. 483-490, vol. 169:6.

Tharion et al., "Energy Expenditure and Water Turnover Assessed by Doubly Labeled Water during Manual Work in a Dry and Warm Environment", Journal of the Human-Environmental System, 2004, pp. 11-17, vol. 7:1.

Tharion et al., "Energy requirements of military personnel", Appetite, 2005, pp. 47-65, vol. 44.

Tharion et al., "Total energy expenditure estimated using a foot-contact pedometer", Med Sci Monit, 2004, pp. CR504-509, vol. 10:9.

Thompson et al., "Dietary Assessment Resource Manual", J. Nutr., 1994, pp. 2245S-2317S, vol. 124.

Tomasi et al., "Bilateral Filtering for Gray and Color Images", Proceedings for the 1998 IEEE International Conference on Computer Vision, 1998, pp. 839-846.

Yao et al., "Error Analysis of a Dimension Estimation Approach", Proc 36th Northeast Biomedical Engineering Conference, 2010, pp. 1-2.

Yao et al., "Food Dimension Estimation From a Single Image Using Structured Lights", Submitted to the Graduate Faculty of the Swanson School of Engineering, 2010, pp. i-xi and 1-96.

Yue, "Dimensional Measurement of Objects in Single Images Independent From Restrictive Camera Parameters", Submitted to the Graduate Faculty of the Swanson School of Engineering, 2010, pp. i-xi and 1-59.

Yue et al., "Food Volume Estimation Using a Circular Reference in Image-Based Dietary Studies", Proc 36th Northeast Biomedical Engineering Conference, 2010, pp. 1-2.

Zhang et al., "A Flexible New Technique for Camera Calibration", IEEE Transactions on Pattern Analysis and Machine Intelligence, 2000, pp. 1330-1334, vol. 22:11.

Zhang et al., "A PDA-based Sign Translator", Proceedings of 4th IEEE International Conference on Multimodal Interfaces, 2002, pp. 217-222.

Zhang et al., "Carried Load Measurement Based on Gait Analysis and Human Kinetics", Congress on Image and Signal Processing, 2008, pp. 104-107.

Zhang et al., "Food Volume Estimation From a Single Image Using Virtual Reality Technology", Submitted to the Graduate Faculty of Swanson School of Engineering, 2010, pp. i-x and 1-69.

Zhang et al., "Improved Carrying Load Measurement Using Video-Based Gait Analysis", Proc. 16th International conference on Mechanics in Medicine and Biology, 2008, pp. 1-2.

Zhang et al., "Load Measurement Based on Gait Analysis", Proc. IEEE 34th Northeast Biomedical Engineering Conference, 2008, pp. 1-2.

Zhang et al., "Measurement of Human Daily Physical Activity", Obesity Research, 2003, pp. 33-40, vol. 11:1.

Zhang et al., "Physical Activity Recognition Based on Motion in Images Acquired by a Wearable Camera", Neurocomputing, 2011, pp. 2184-2192, vol. 74:12-13.

Zhang et al., "Recognizing Physical Activity from Ego-motion of a Camera", 32nd Annual International Conference of the IEEE EMBS, 2010, pp. 5569-5572.

Zhang et al., "Segmentation for Efficient Browsing of Chronical Video Recorded by a Wearable Device", Proc 36th Northeast Biomedical Engineering Conference, 2010, pp. 1-2.

(56) References Cited

OTHER PUBLICATIONS

Zhang et al., "The design and realization of a wearable embedded device for dietary and physical activity monitoring", The 3rd International Symposium on Systems and Control in Aeronautics and Astronautics, 2010, pp. 1-4.
Zhang et al., "Weight measurement using image-based pose analysis", Progress in Natural Science, 2008, pp. 1507-1512, vol. 18.
Zheng et al., "Lung Sound Pattern Analysis for Anesthesia Monitoring", 2005 American Control Conference, 2005, pp. 1563-1568.
Zhu et al., "The Use of Mobile Devices in Aiding Dietary Assessment and Evaluation", IEEE J Sel Top Signal Process, 2010, pp. 756-766, vol. 4:4.
Yoshida et al., "Development of Infrared Lip Movement Sensor for Spoken Word Recognition", Systemics, Cybernetics and Informaticis, 2007, vol. 5:6.
Chen et al., "PFID: Pittsburgh Fast-Food Image Dataset", 16th IEEE International Conference on Image Processing, 2009, pp. 1-4.
Thompson, "Overweight and Obesity: A Major Public Health Issue, Prevention Report", U.S. Department of Health and Human Services, 2001, pp. 1-18, vol. 16:1, http://odphp.osophs.dhhs.gov/pubs/prevrpt/.
Trabulsi et al., "Evaluation of dietary assessment instruments against doubly labeled water, a biomaker of habitual energy intake", Am J Physiol Endocrinol Metal., 2001, pp. 891-899, vol. 281.
Turconi et al., "An evaluation of a colour food photography atlas as a tool for quantifying food portion size in epidemiological dietary surveys", Europoean Journal of Clinical Nutrition, 2005, pp. 923-931, vol. 59.
Tuschl et al., "Energy expenditure and everyday eating behavior in healthy young women", Am J Clin Nutr, 1990, pp. 81-86, vol. 52.
U.S. Department of Agriculture and Agricultural Research Service, "USDA National Nutrient Database for Standard Reference, Release 19", 2006, www.ars.usda.gov/ba/bhnrc/ndl.
U.S. Department of Agriculture and Agricultural Research Service, "USDA National Nutrient Database for Standard Reference, Release 20", 2008, www.ars.usda.gov/ba/bhnrc/ndl.
U.S. Department of Health and Human Services, "Strategic Plan for NIH Obesity Research", National Institutes of Health, 2011, NIH Publication No. 11-5493.
U.S. Department of Labor, Bureau of Labor Statistics, "American Time Use Survey", USDL 06-1276, Washington, D.C., Jul. 27, 2006.
Vanderschoot et al., "Biaxial Esophagus Microphone Recording of Lung Sound", Annual International Conference of the IEEE Engineering in Medicine and Biology Society, 1991, pp. 1631-1632, vol. 13:4.
Vathsangam et al., "Energy Estimation of Treadmill Walking using On-body Accelerometers and Gyroscopes", 32nd Annual International Conference of the IEEE EMBS, 2010, pp. 6497-6501.
Velthuis-Te Wierk et al., "Impact of a moderately energy-restricted diet on energy metabolism and body composition in non-obese men", International Journal of Obesity, 1995, pp. 318-324, vol. 19.
Vincent, "Morphological Grayscale Reconstruction in Image Analysis: Applications and Efficient Algorithms", IEEE Transactions on Image Processing, 1993, pp. 176-201, vol. 2:2.
Vincent et al., "Watersheds in Digital Spaces: An Efficient Algorithm Based on Immersion Simulations", IEEE Transactions on Pattern Analysis and Machine Intelligence, 1991, pp. 583-589, vol. 13:6.
Viola et al., "Robust Real-Time Face Detection", International Journal of Computer Vision, 2004, pp. 137-154, vol. 57:2.
Viola et al., "Rapid Object Detection using a Boosted Cascade of Simple Features", Accepted Conference on Computer Vision and Pattern Recognition, 2001, pp. 511-517.
Vitabile et al., "Road Signs Recognition Using a Dynamic Pixel Aggregation Technique in the HSV Color Space", IEEE, 2001, pp. 572-577.
Wang et al., "A DCT-based MPEG-2 Transparent Scrambling Algorithm", IEEE Transactions on Consumer Electronics, 2003, pp. 1208-1213, vol. 49:4.

Wang et al., "Continuous Intro-Operative Respiratory Auscultation in Anesthesa", IEEE, 2003, pp. 1002-1005.
Wang et al., "Image Registration for an Imaging System On-Board Fast Moving Military Vehicle", IEEE, 2000, pp. 239-243.
Wang et al., "Modeling Background from Compressed Video", Proceedings 2nd Joint IEEE International Workshop on VS-PETS, 2005, pp. 161-168.
Wang et al., "Representing Moving Images with Layers", IEEE Transactions on Image Processing, 1994, pp. 625-638, vol. 3:5.
Ward et al., "Accelerometer Use in Physical Activity: Best Practices and Research Recommendations", Medicine & Science, 2005, pp. S582-S588.
Wareham et al., "The assessment of physical activity in individuals and populations: Why try to be more precise about how physical activity is assessed?", International Journal of Obesity, 1998, pp. S30-S38, vol. 22.
Warziski et al., "Changes in self-efficacy and dietary adherence: the impact on weight loss in the PREFER study", J Behav Med, 2008, pp. 81-92, vol. 31.
Webster "Medical Instrumentation: Application and Design", Third Edition, Wiley, 1998.
Weiss et al., "Automatic Food Documentation and Volume Computation using Digital Imaging and Electronic Transmission", J Am Diet Assoc., 2010, pp. 1-5, vol. 110:1.
Wells et al., "Precision and accuracy in a metabolic monitor for indirect calorimetry", European Journal of Clinical Nutrition, 1998, pp. 536-540, vol. 52.
Wessel et al., "Optimization of an Implantable Volume Conduction Antenna", Proceedings of the 26th Annual International Conference of the IEEE EMBS, 2004, pp. 4111-4114.
Westerterp et al., "Physical activity assessment with accelerometers", International Journal of Obesity, 1999, pp. S45-S49, vol. 23, Suppl. 3.
Westerterp, "Physical Activity Assessment With Accelerometers in Children", Indian Pediatrics, 2009, pp. 1053-1054, vol. 46.
Wu et al., "Fast Food Recognition From Videos of Eating for Calorie Estimation", Proc. IEEE ICME, 2009, pp. 1210-1213.
World Wide Web Consortium W3C, "Synchronized Multimedia Integration Language (SMIL) 1.0 Specification", Jun. 15, 1998, http://www.w3.org/TR/1998/REC-smil-19980615.
Xu et al., "Content-Based Video Coding for Remote Monitoring of Neurosurgery", Proceedings of the 26th Annual International Conference of the IEEE EMBS, 2004, pp. 3136-3139.
Xu et al., "Content-Based Video Preprocessing for Remote Monitoring of Neurosurgery", Proceedings of the 1st Distributed Diagnosis and Home Healthcare (D2H2) Conference, 2006, pp. 67-70.
Xu et al., "Multi-Channel Video for Patient Monitoring based on DCT Compositing", IEEE, 2004, pp. 63-64.
Xu et al., "A Region-Based Video Coding Method for Remote Monitoring of Neurosurgery", IEEE, 2005, pp. 1-3.
Yadollahi et al., "A Robust Method for Estimating Respiratory Flow Using Tracheal Sounds Entropy", IEEE Transactions on Biomedical Engineering, 2006, pp. 662-668, vol. 53:4.
Yan et al., "A Discriminative Learning Framework with Pairwise Constraints for Video Object Classification", Proceedings of the 2004 IEEE Computer Society Conference on Computer Vision and Pattern Recognition, 2004, pp. 284-291.
Yan et al., "A Discriminative Learning Framework with Pairwise Constraints for Video Object Classification", IEEE Transactions on Pattern Analysis and Machine Intelligence, 2006, pp. 578-593.
Yan et al., "Automatically Labeling Video Data Using Multi-class Active Learning", Proceedings of the Ninth IEEE International Conference on Computer Vision, 2003, pp. 516-523.
Yang et al., "A PDA-based Face Recognition System", Proceedings of the 6th IEEE Workshop on Applications of Computer Vision, 2002, pp. 19-23.
Yang et al., "An Adaptive Multimodal Interface for Wireless Applications", Proceedings of 2nds International Symposium on Wearable Computers, 1998, pp. 172-173.
Yang et al., "An Automatic Sign Recognition and Translation System", PUI, 2001, pp. 1-8.

(56) References Cited

OTHER PUBLICATIONS

Yang et al., "Automatic Dietary Assessment from Fast Food Categorization", Proc. IEEE 34th Northeast Biomedical Engineering Conference, 2008, pp. 1-2.
Yang et al., "Face as an Index: Knowing Who is Who Using PDA", Inc. Int J Imaging Syst Technol., 2003, pp. 33-41, vol. 13.
Yang et al., "Interactive Dietary Assessment From Video", 16th International Conference on Mechanics in Medicine and Biology, 2008, pp. 1-2.
Yang et al., "Smart Sight: A Tourist Assistant System", Proceedings of 3rd International Symposium on Wearable Computers, 1999, pp. 73-78.
Yao et al., "A Laser Based Depth Measurement Method for Digital Imaging of Close-Up Objects", 16th International Conference on Mechanics in Medicine and Biology, 2008.
Yao et al., "A Video-based Algorithm for Food Intake Estimation in the Study of Obesity", Proceedings of the 2007 IEEE 33rd Annual Northeast Bioengineering Conference, 2007, pp. 298-299.
Yao et al., "A Video Processing Approach to the Study of Obesity", Proceedings of the 2007 IEEE International Conference on Multimedia & Expo, 2007, pp. 1727-1730.
Liu et al., "Change Detection in Epilepsy Monitoring Video Based on Markov Random Field Theory", IEEE, 2004, pp. 63-66.
Liu et al., "Patient Tracking for Video/EEG Monitoring Based on Change Detection in DCT Doman", IEEE, 2005, pp. 1-2.
Liu et al., "Specialized Video and Physiological Data Coding System for Remote Monitoring", Proceedings of the 2006 IEEE International Conference on Multimedia & Expo., 2006, pp. 2001-2004.
Ma et al., "EdgeFlow: A Technique for Boundary Detection and Image Segmentation", IEEE Trans Image Processing, 2000, pp. 1375-1388.
Maffei et al., "Leptin levels in human and rodent: Measurement of plasma leptin and ob RNA in obese and weight-reduced subjects", Nature Medicine, 1995, pp. 1155-1161, vol. 1:11.
Malkin et al., "Directing Attention in Online Aggregate Sensor Streams Via Auditory Blind Value Assignment", Proceedings of the 2006 IEEE International Conference on Multimedia & Expo, 2006, pp. 2137-2140.
Malkin et al., "Multimodal Estimation of User Interruptibility for Smart Mobile Telephones", Proceeding of the 8th International Conference on Multimodal Interfaces, 2006, pp. 118-125.
Manjunath et al., "Texture Features for Browsing and Retrieval of Image Data", IEEE Transactions on Pattern Analysis and Machine Intelligence, 1996, pp. 837-842, vol. 18:8.
Mayagoitia et al., "Accelerometer and rate gyropscope measurement of kinematics: an inexpensive alternative to optical motion analysis systems", Journal of Biomechanics, 2002, pp. 537-542, vol. 35.
Meier et al., "Video Segmentation for Content-Based Coding", IEEE Transactions on Circuits and Systems for Video Technology, 1999, pp. 1190-1203, vol. 9:8.
MiniSun, "A Device for Analyzing Body Motion", IDEEA Overview, http://minisun.com/ideea_overview.asp, as early as Apr. 2007.
Moscheni et al., "Spatiotemporal Segmentation Based on Region Merging", IEEE Transactions on Pattern Analysis and Machine Intelligence, 1998, pp. 897-915, vol. 20:9.
Must et al., "The Disease Burden Associated With Overweight and Obesity", JAMA, 1999, pp. 1523-1529, vol. 282:16.
Nardi et al., "Turning Away from Talking Heads: The Use of Video-as-Data in Neurosurgery", Interchi, 1993, pp. 327-334.
Nie et al., "Automatic Detection of Dining Plates in Digital Video", Proc 36th Northeast Biomedical Engineering Conference, 2010, pp. 1-2.
Nie et al., "Automatic Detection of Dining Plates for Image-Based Dietary Evaluation", 32nd Annual International Conference of the IEEE Engineering in Medicine and Biology Society, 2010, pp. 1-4.
Neilsen et al., "Patterns and Trends in Food Portion Sizes, 1977-1998", JAMA, 2003, pp. 450-453, vol. 289:4.
NIH 1R01EB002309-01, "Video Compression for Remote Monitoring of Neurosurgery". (Abstract Only).
NIH 2-R01-NS/MH38494-04, "Video-EEG Data Compression". (Abstract Only).
NIH Grant R01EB002099, "Data Communication and Power Delivery for Implantable Micro Devices". (Abstract Only).
Otsu, "A Threshold Selection Method from Gray-Level Histograms", IEEE Transactions on Systems, Man, and Cybermetics, 1979, pp. 62-66, vol. SMC-9:1.
Pazarci et al., "A MPEG2-Transparent Scrambling Technique", IEEE, 2002, pp. 345-355.
Peng et al., "Object-Based Video Representation for Remote Patient", Proceedings of the 1st Distributed Diagnosis and Home Healthcare (D2H2) Conference, 2006, pp. 83-86.
Perlman et al., "Respiratory and Acoustic Signals Associated with Bolus Passage during Swallowing", Dysphagia, 2000, pp. 89-94, vol. 15.
Pingali et al., "Electronic Chronicles: Empowering Individuals, Groups, and Organizations", IEEE, 2005, pp. 1540-1544.
Plasqui et al., "Physical Activity Assessment With Accelerometers: An Evaluation Against Doubly Labeled Water", Obesity, 2007, pp. 2371-2379, vol. 15:10.
Pon et al., "A Medical EEG/Video Multimedia Content Description System", IEEE, 2004, pp. 592-595.
Pon et al., "Adaptive Separation of Background Activity and Transient Phenomenon in Epileptic EEG Using Mathematical Morphology and Wavelet Transforms", Proceedings of the 22nd Annual EMBS International Conference, 2000, pp. 1583-1585.
Pon et al., "The Bi-Directional Spike Detection in EEG Using Mathematical Morphology and Wavelet Transform", IEEE, 2002, pp. 1512-1515.
Pon et al., "Analysis of Heart Rate Changes Associated with Ictal Activity", Proceedings of the 22nd Annual EMBS International Conference, 2000, pp. 68-70.
Pon et al., "Interictal Spike Analysis Using Stochastic Point Process", Proceedings of the Fourth International Symposium on Uncertainly Modeling and Analysis (ISUMA '03), 2003, pp. 262-267.
Pon et al., "Separation of Spiky Transients in EEG/MEG Using Morphological Filters in Multi-Resolution Analysis", Ph.D. Thesis, Department of Electrical Engineering, University of Pittsburgh, 2002.
Prentice et al., "High levels of energy expenditure in obese women", British Medical Journal, 1986, pp. 983-987, vol. 292.
Press et al., "Numerical Recipes in C: The Art of Scientific Computing Second Edition", 1992, Cambridge University Press, New York, NY.
Racette et al., "Relative dilution spaces of 2H- and 18O-labeled water in humans", The American Physiological Society, 1994, pp. E585-E590.
Rappaport, "Implications of the exposome for exposure science", Journal of Esposure Science and Environmental Epidemiology, 2011, pp. 5-9, vol. 21.
Rhee, "Internet Security: Cryptographic principles, algorithms and protocols", Wiley, 2003 pp. 57-75 and 162-172.
Rogers et al., "The CLEF Chronicle: Patient Histories derived from Electronic Health Records", Proceedings of the 22nd International Conference on Data Engineering Workshops, 2006.
Rudney et al., "The Prediction of Saliva Swallowing Frequency in Humans From Estimates of Saliva Swallowed", Archs Oral Biol, 1995, pp. 507-512; vol. 40:6.
Sarkar et al., "The HumanID Gait Challenge Problem: Data Sets, Performance, and Analysis", IEEE Transactions on Pattern Analysis and Machine Intelligence, 2005, pp. 162-177, vol. 27:2.
Schatzkin et al., "A comparison of a food frequency questionnaire with a 24-hour recall for use in an epidemiological cohort study: results from the biomarker-based Observing Protein and Energy Nutrition (OPEN) study", International Journal of Epidemiology, 2003, pp. 1054-1062, vol. 32:6.
Scher et al., "Cardiorespiratory Behavior during Sleep in Full-Term and Preterm Neonates at Comparable Postconceptional Term Ages", Pediatric Research, 1994, pp. 738-744, vol. 36:6.

(56) References Cited

OTHER PUBLICATIONS

Scher et al., "Computer Analysis of EEG-Sleep in the Neonate: Methodological Considerations", Journal of Clinical Neurophysiology, 1990, pp. 417-441, vol. 7:3.

Scher et al., "Comparisons of EEG spectral and correlation measures between healthy term and preterm infants", Pediatric Neurology, 1994, pp. 104-108, vol. 10:2.

Schoeller, "How Accurate Is Self-Reported Dietary Energy Intake?", Nutrition Reviews, 1990, pp. 373-379, vol. 48:10.

Schoeller et al., "How much physical activity is needed to minimize weight gain in previously obese women?" Am J Clin Nutr, 1997, pp. 551-556, vol. 66.

Schoeller et al., "Inaccuracies in self-reported intake identified by comparison with the doubly labelled water method", Can J Physiol Pharmacol., 1990, pp. 941-949, vol. 68:7.

Schoeller, "Measurement of Energy Expenditure in Free-Living Humans by Using Doubly Labeled Water", J Nutr., 1988, pp. 1278-1289, vol. 129:20.

Schoeller, "Recent Advances from Application of Doubly Labeled Water to Measurement of Human Energy Expenditure", The Journal of Nutrition, 1999, pp. 1765-1768, vol. 129.

Schutz et al., "Assessment of Free-Living Physical Activity in Humans: An Overview of Currently Available and Proposed New Measures", Obesity Research, 2001, pp. 368-379, vol. 9:6.

Chen et al., "Expand Training Set for Face Detection by GA Re-sampling", Proceedings of the Sixth IEEE International Conference on Automatic Face and Gesture Recognition, 2004, pp. 73-78.

Chen et al., "Mining Appearance Models Directly from Compressed Video", Proceedings of the 12th AnCM SIGKDD International Conference on Knowledge Discovery and Data Mining, 2006, pp. 1-9.

Chen et al., "Mining Appearance Models Directly From Compressed Video", IEEE Transactions on Multimedia, 2008, pp. 268-276, vol. 10:2.

Chen et al., "Multimodal Detection of Human Interaction Events in a Nursing Home Environment", Proceedings of ACM International Conference on Multimodal Interface, 2004, pp. 82-89.

Chen et al., "Online Learning of Region Confidences for Object Tracking", 10th IEEE International Conference on Computer Vision, 2005, pp. 1-8.

Chen et al., "Tools for Protecting the Privacy of Specific Individuals in Video", EURASIP Journal on Advances in Signal Processing, 2007, pp. 1-9, vol. 2007.

Chen et al., "Towards Automatic Analysis of Social Interaction Patterns in a Nursing Home Environment from Video", 6th ACM SIGMM Int'l Workshop on Multimedia Information Revival, in Proc. of ACM Multimedia, 2004, pp. 283-290.

Choi et al., "Effects of chronic fenfluramine administration on hypothalamic neuropeptide mRNA expression", Brain Research, 2006, pp. 83-86, vol. 1087.

Choi et al., "Intermittent, chronic fenfluramine administration to rats repeatedly suppresses food intake despite substantial brain serotonin reductions", Brain Research, 2002, pp. 30-39, vol. 928.

Christel, "Windowing Time in Digital Libraries", Proc. ACM/IEEE-CS Joint Conference on Digital Libraries, 2006, pp. 190-191.

Clark et al., "Energy metabolism in free-living, 'large-eating' and 'small-eating' women: studies using 2H218O", British Journal of Nutrition, 1992, pp. 21-31, vol. 72.

Clark (ed.) (1999), "XSL Transformations (XSLT)" World Wide Webb Consortium (W3C) Recommendation Nov. 16, 1999.

Coates et al., "Gastric Bypass Surgery for Morbid Obesity Leads to an Increase in Bone Turnover and a Decrease in Bone Mass", The Journal of Clinical Endocrinology & Metabolism, 2004, pp. 1061-1065, vol. 89:3.

Conroy et al., "Physical Activity Self-Monitoring and Weight Loss: 6-Month Results of the SMART Trial", Medicine & Science in Sports & Exercise, 2010, pp. 1568-1574.

Crouter et al., "Validity of 10 Electronic Pedometers for Measuring Steps, Distance, and Energy", Medicine & Science in Sports * Exercise, 2003, pp. 1455-1460.

Delaney et al., "Energy expenditure and substrate oxidation predict changes in body fat in children", Am J Clin Nutr, 2006, pp. 862-870, vol. 84.

Delaney et al., "Energy expenditure in African American and white boys and girls in a 2-y follow-up of the Baton Rouge Children's Study", Am J Clin Nutr, 2004, pp. 268-273, vol. 79.

Delaney et al., "Energy expenditure in preadolescent African American and white boys and girls: the Baton Rouge Children's Study", Am J Clin Nutr, 2002, pp. 705-713, vol. 75.

Delaney et al., "Field use of D218O to measure energy expenditure of soliers at different energy intakes", J. Appl. Physiol., 1989, pp. 1922-1929, vol. 67:5.

Dittmann et al., "Enabling Technology for the Trading of MPEG-encoded Video", Lecture Notes in Computer Science, 1997, pp. 314-324, vol. 1270.

De Jonge et al., "Validation study of energy expenditure and intake during calorie restriction using doubly labeled water and changes in body composition", Am J Clin Nutr, 2007, pp. 73-79, vol. 85.

Elad, "On the Origin of the Bilateral Filter and Ways to Improve It", IEEE Transactions on Image Processing, 2002, pp. 1141-1151, vol. 11:10.

Ellenby et al., "Uncoupling and Recoupling of Autonomic Regulation of the Heart Beat in Pediatric Septic Shock", Shock, 2001, pp. 274-277, vol. 16:4.

Eng, "Sample Size Estimation: A Glimpse beyond Simple Formulas", Radiology, 2004, pp. 606-612, vol. 230.

Eng, "Sample Size Estimation: How Many Individuals Should Be Studied?", Radiology, 2003, pp. 309-313, vol. 227.

Ershow et al., "Engineering Approaches to Energy Balance and Obesity: Opportunities for Novel Collaborations and Research", Journal of Diabetes Science and Technology, 2007, pp. 95-105, vol. 1:1.

Farooqi et al., "Effects of Recombinant Leptin Therapy in a Child With Congenital Leptin Deficiency", Brief Report, 1999, pp. 879-884, vol. 341:12.

Faugeras et al., "Complete Dense Stereovision using Level Set Methods", INRIA, France and MIT AI-Lab, pp. 1-15.

Fernstrom et al., "Long-term Changes in Blood Pressure in Extremely Obese Patients Who Have Undergone Bariatric Surgery", Arch Surg, 2006, pp. 276-283, vol. 141.

Ferrucci et al., "Building an example application with the Unstructured Information Management Architecture", IMB Systems Journal, 2004, pp. 455-475, vol. 43:3.

Ferrucci et al., "UIMA: An Architectural Approach to Unstructured Information Processing in the Corporate Research Environment", Journal of Natural Language Engineering, 2004, pp. 1-26.

Firmin et al., "Non-Invasive Monitoring of Reflexive Swallowing", Speech Hearing and Language: work in progress, 1997, pp. 171-184, vol. 10.

Flegal et al., "Prevalence and Trends in Obesity Among US Adults, 1999-2000", JAMA, 2002, pp. 1723-1727, vol. 288:14.

Foutrakis et al., "Saccular Aneurysm Formation in Curved and Bifurcating Arteries", AJNR Am J Neuroradiol, 1999, pp. 1309-1317, vol. 20.

Frankenfield et al., "Comparison of Predictive Equations for Resting Metabolic Rate in Healthy Nonobese and Obese Adults: A Systematic Review", Journal of the American Dietetic Association, 2005, pp. 775-789, vol. 105:5.

Freedman et al., "Energy Minimization via Graph Cuts: Settling What is Possible", IEEE Computer Society Conference on Computer Vision and Pattern Recognition, 2005, pp. 939-946, vol. 2.

Freedman et al., "Trends and Correlates of Class 3 Obesity in the United States From 1990 Through 2000", JAMA, 2002, pp. 1758-1761, vol. 288:14.

Freedson et al., "Objective Monitoring of Physical Activity Using Motion Sensors and Heart Rate", Research Quarterly for Exercise and Sport, 2000, pp. 21-29, vol. 71:2.

Friedl, "Bioenergetics of Animal Locomotion: Lessons for Expedient Monitoring in Human Fitness and Weight Management", Diabetes Technology & Therapeutics, 2004, pp. 83-86, vol. 6.

(56) References Cited

OTHER PUBLICATIONS

Friedman et al., "Leptin and the regulation of body weight in mammals", Nature, 1998, pp. 763-770, vol. 395.
Friedman, "Obesity in the new millennium", Nature, 2000, pp. 632-634, vol. 404.
Frykman et al., "Effects of a 3-Month Endurance Event on Physical Performance and Body Composition: The G2 Trans-Greenland Expedition", Wilderness and Environmental Medicine, 2003, pp. 240-248, vol. 14.
Gao et al., "Articulated Motion Modeling for Activity Analysis", Third International Conference on Image and Video Retrieval, Workshop on Articulated and Nonrigid Motion, 2004, pp. 1-9.
Gao et al., "Combining Motion Segmentation with Tracking for Activity Analysis", Proceedings of the Sixth IEEE International Conference on Automatic Face and Gesture Recognition, 2004, pp. 699-704.
Gao et al., "Dining Activity Analysis Using a Hidden Markov Model", 17th International Conference on Pattern Recognition, 2004, pp. 1-4.
Gemmell et al., "MyLifeBits: Fulfilling the Memex Vision", ACM Multimedia, 2002, pp. 235-238.
Gephart et al., "Nonlinear Dynamics of Heart Rate in Epilepsy", Proceedings of the 22nd Annual EMBS International Conference, 2000, pp. 2903-2905.
Gonzalez et al., "Digital Image Processing", Addison-Wesley Publishing Company, 1993.
Goran et al., "Total Energy Expenditure and Energy Requirements in Healthy Elderly Persons", Metabolism, 1992, pp. 744-753, vol. 41:7.
Goris et al., "Postabsorptive respiratory quotient and food quotient—an analysis in lean and obese men and women", European Journal of Clinical Nutrition, 2004, pp. 546-550, vol. 54.
Agarwal et al., "Dense Stereo Matching over the Panum Band", IEEE Transactions on Pattern Analysis and Machine Intelligence, Mar. 2010, pp. 416-430, vol. 32:3.
Ainsworth et al., "Compendium of Physical Activities: an update of activity codes and MET intensities", Medicine & Science in Sports & Excercise, 2000, pp. S498-S516.
Andre et al., "Recent Advances in Free-Living Physical Activity Monitoring: A Review", Journal of Diabetes Science and Technology, Sep. 2007, pp. 760-767, vol. 1, Issue 5.
Akgul et al., "Characterization of Sleep Spindles Using Higher Order Statistics and Spectra" IEEE Transactions on Biomedical Engineering, Aug. 2000, pp. 977-1009, vol. 47:8.
Armanios et al., "Telomerase Mutations in Families with Idiopathic Pulmonary Fibrosis", The New England Journal of Medicine, Mar. 29, 2007, pp. 1317-1326.
Baker-Fulco et al., "Dietary Intakes of Female and Male Combat Support Hospital Personnel Subsisting on Meal-Focused or Standard Versions of the Meal, Ready-to-Eat", Sep. 2002, U.S. Army Medical Research and Materiel Command Technical Report No. T-02/23.
Bandini et al., "Validity of reported energy intake in obese and nonobese adolescents", Am J. Clin Nutr., 1990, pp. 421-425, vol. 52.
Barsh et al., "Genetics of body-weight regulation", Nature, Apr. 6, 2000, pp. 644-651, vol. 404.
Bates et al., "Analysis of Multi-Channel Subdural EEG by Recurrent Neural Networks", Applied Research in Uncertainty Modeling and Analysis, 2005, pp. 139-159.
Bates et al., "Detection of Seizure Foci by Recurrent Neural Networks", Proceedings of the 22nd Annual EMBS Internation Conference, 2000, pp. 1377-1379.
Bates et al., "Seizure Detection by Recurrent Backpropagation Neural Network Analysis", Proceedings of the Fourth International Symposium on Uncertainty Modeling and Analysis, 2003, pp. 312-317.

Bathalon et al., "Psychological measures of eating behavior and the accuracy of 3 common dietary assessment methods in healthy postmenopausal women", Am J Clin Nutr, 2000, pp. 739-745, vol. 71.
Bell, "A Personal Digital Store", Communications of the ACM, 2001, pp. 86-91, vol. 44:1.
Bell et al., "The Revolution Yet to Happen", Beyond Calculation: The Next Fifty Years of Computing, pp. 5-32.
Bilmes et al., "A Gentle Tutorial of the EM Algorithm and its Application to Parameter Estimation for Gaussian Mixture and Hidden Markov Models", International Computer Science Institute, 1998, pp. 1-13.
Black et al., "Validation of dietary intakes of protein and energy against 24 hour urinary N and DLW energy expenditure in middle-aged women, retired men and post-obese subjects: comparisons with validation against presumed energy requirements", European Journal of Cliniacl Nutrition, 1997, pp. 405-413, vol. 51.
Blundell, "What foods do people habitually eat? A dilemma for nutrition, an enigma for psychology", Am J Clin Nuitr, 2000, pp. 3-5, vol. 71.
Bodo et al., "A scrambling method based on disturbance of motion vector", Multimedia, 2002, pp. 89-90.
Borrell, "Every Bite You Take", Nature, 2011, pp. 320-322, vol. 470.
Bouchard et al., "The Response to Long-Term Overfeeding in Identical Twins", The New England Journal of Medicine, 1990, pp. 1477-1492, vol. 322:21.
Boushey et al., "Use of technology in children's dietary assessment", Eur J Clin Nutr, 2009, pp. S50-S57, vol. 63.
Bouguet, "Camera Calibration Toolbox for Matlab", http://www.vision.caltech.edu/bouguetj/calib_doc/index.html, 2008.
Boykov et al., "An Experimental Comparison of Min-Cut/Max-Flow Algorithms for Energy Minimization in Vision", IEEE Transactions on PAMI, 2004, pp. 1124-1137, vol. 26:9.
Boyle et al., "The Effects of Filtered Video on Awareness and Privacy", Proc. ACM CSCW, 2000, pp. 1-10.
Bray et al., "Evalution of body fat in fatter and leaner 10-y-old African American and white children: the Baton Rouge Children's Study", Am J Clin Nutr, 2001, pp. 687-702, vol. 73.
Bray et al., "The Influence of Different Fats and Fatty Acids on Obesity, Insulin Resistance and Inflammation", American Society for Nutritional Sciences, 2002, pp. 2488-2491.
Bray et al., World Wide Web Consortium (W3C) Recommendation: Extensible Markup Language (XML) 1.0., Feb. 10, 1998.
Breum et al., "Twenty-four-hour plasma tryptophan concentrations and ratios are below normal in obese subjects and are not normalized by substantial weight reduction", Am J Clin Nutr, 2003, pp. 1112-1118, vol. 77.
Buhl et al., "Unexplained disturbance in body weight regulation: Diagnostic outcome assessed by doubly labeled water and body composition analyses in obese patients reporting low energy intakes", Journal of the American Dietetic Association, 1995, pp. 1393-1400.
Burke et al., "Ancillary study to the PREFER trial: A descriptive study of participants' patterns of self-monitoring-rationale, design and preliminary experiences", Contemporary Clinical Trials, 2006, pp. 23-33, vol. 27.
Burke et al., "Development and Testing of the Cholesterol-Lowering Diet Self Efficacy Scale", European Journal of Cardiovascular Nursing, 2003, pp. 265-273, vol. 2.
Burke et al., "Evaluation of the Shortened Cholesterol-Lowering Diet Self-Efficacy Scale", European Journal of Cardiovascular Nursing, 2006, pp. 264-274, vol. 5.
Burke et al., "Experiences of Self-Monitoring: Successes and Struggles During Treatment for Weight Loss", Qualitative Health Research, 2009, pp. 815-828, vol. 19:6.
Burke et al., "Self-Monitoring Dietary Intake: Current and Future Practices", Journal of Renal Nutrition, 2005, pp. 281-290, vol. 15:3.
Burke et al., "Self-Monitoring in Weight Loss: A Systematic Review of the Literature", J Am Diet Assoc., 2011, pp. 92-102, vol. 111:1.
Burke et al., "SMART trial: A randomized clinical trial of self-monitoring in behavioral weight management-design and baseline findings", Contemp Clin Trials, 2009, pp. 540-551, vol. 30:6.

(56) References Cited

OTHER PUBLICATIONS

Burke et al., "The Effect of Electronic Self-Monitoring on Weight Loss and Dietary Intake: A Randomized Behavioral Weight Loss Trial", Obesity (Silver Spring), 2011, pp. 338-344, vol. 19:2.
Burke et al., "Using Instrumented Paper Diaries to Document Self-Monitoring Patterns in Weight-Loss", Contemp Clin Trials, 2008, pp. 182-193, vol. 29:2.
Campfield et al., "Recombinant Mouse OB Protein: Evidence for a Peripheral Signal Linking Adiposity and Central Neural Networks", Science, New Series 1995, pp. 546-549, vol. 269:5223.
Caramori et al., "Gene-environment interactions in the development of chronic obstructive pulmonary disease current Opinion", Allergy and Clinical Immunology, 2006, pp. 323-328, vol. 6.
Caslake et al., "Effect of sex and genotype on cardiovascular biomarker response to fish oils: the FINGEN Study", Am J Clin Nutr, 2008, pp. 619-629, vol. 88.
Castellani et al., "Body Fluid Regulation in a Simulated Disabled Submarine: Effecs of Cold, Reduced O2, and Elevated CO2", Aviation, Space, and Environmental Medicine, 2005, pp. 753-759, vol. 76(8).
Castellani et al., "Energy Expenditure in Men and Women during 54 h of Exercise and Caloric Deprivation", Medicine & Science in Sports & Exercise, 2006, pp. 894-900.
Champagne et al., "Energy intake and energy expenditure: A controlled study comparing dietitians and non-dietitians", J. Am Diet Assoc., 2002, pp. 1428-1432, vol. 102:10.
Chang et al., "People Identification With Limited Labels in Privacy-Protected Video", International Conference on Multimedia & Expo, 2006, pp. 1-4.
Charles et al., "Statistical Reduction of EEG Data" Proceedings of the 22nd Annual EMBS International Conference, 2000, pp. 1394-1395.
Chen et al., "A Study of Detecting Social Interaction with Sensors in a Nuring Home Environment", International Conference on Computer Vision workshop on Human-Computer Interaction, In conjunction with the Tenth IEEE International Conference on Computer Vision, 2005, pp. 1-12.
Chen et al., "Activity Analysis in Privacy-Protected Video", http://www.informedia.cs.cmu.edu/documents/T-MM_Privacy_J2c.pdf.
Chen et al., "Detecting Social Interaction of Elderly in a Nursing Home Environment", ACM Transactions on Multimedia Comuting, Communications, and Applications, 2007, pp. 1-36, Article 6.
Chen et al., "Exploiting High Dimensional Video Features Using Layered Gaussian Mixture Models", The 18th International Conference on Pattern Recognition, 2006, pp. 1078-1081.
Goris et al., "Undereating and underrecording of habitual food intake in obese men: selective underreporting of fat intake", Am J Clin Nutr, 2000, pp. 130-134, vol. 71.
Greiner et al., "Privacy Protection in an Electronic Chronicle System", Proceedings of the 2008 IEEE 34th Annual Northeast Bioengineering Conference, 2008, pp. 1-2, (Abstract).
Guven et al., "Picasso: Pervasive Information Chronicling, Access, Search, and Sharing for Organizations", Proceedings of the 3rd IEEE Int'l Conf. on Pervasive Computing and Communications, 2005, pp. 341-350.
Hammond et al., "The economic impact of obesity in the United States", Diabetes, Metabolic Syndrome and Obesity: Targets and Therapy, 2010, pp. 285-295, vol. 3.
Harper et al., "Time Series Analysis and Sleep Research", IEEE Transactions on Automatic Control, 1974, pp. 932-943, vol. AC-19:6.
Hassoun, "Fundamentals of Artificial Neural Networks", MIT Press, Mar. 27, 1995, Cambridge, Massachusetts.
Hauptmann et al., "Automated Analysis of Nursing Home Observations", IEEE Pervasive Computing, 2004, pp. 15-21.
Heilbronn et al., "Effect of 6-Month Calorie Restriction on Biomarkers of Longevity, Metabolic Adaptation, and Oxidative Stress in Overweight Individuals: A randomized Controlled Trial", JAMA, 2006, pp. 1539-1548, vol. 295:13.
Herodotou et al., "A Color Segmentation Scheme for Object-Based Video Coding", IEEE, 1998, pp. 25-30.
Hiiemae et al., "Mastication, Food Transport, and Swallowing", 1985, pp. 262-290, Belknap Press of Harvard University.
Hintze, "Pass Power Analysis and Sample Size System", User's Guide I, 2000, pp. 1-7, NCSS.
Hitachi Metals America, Ltd. Press Release, "Development of the World's Smallest Accelerometer Sensor", Aug. 23, 2006.
Hoyt et al., "Total Energy Expenditure Estimated Using Foot-Ground Contact Pedometry", Diabetes Technology & Therapeutics, 2004, pp. 71-81, vol. 6:1.
Hu et al., "Comparing Interlaced and Progressive Scans for MPEG Coding of Medical Video", IEEE, 2005, pp. 1-2.
Hughes et al., "Engagement in reading and hobbies and risk of incident dementia: The MoVIES Project", Am J Alzheimers Dis Other Demen., 2010, pp. 432-438, vol. 25:5.
Hui et al., "A Brief Introduction of National Standard of the People's Republic of China 'Mass Center of Chinese Adults'", Proceedings of the 20th Annual International Conference of the IEEE Engineering in Medicine and Biology Society, 1998, pp. 3374-3378, vol. 20:6.
Hunter, "MPEG-7 Behind the Scenes", D-Lib Magazine, 1999, vol. 5:9.
Irwin et al., "Estimation of Energy Expenditure from Physical Activity Measures: Determinants of Accuracy", Obesity Research, 2001, pp. 517-525, vol. 9:9.
Jain, "Multimedia Electronic Chronicles", Media Vision, 2003, pp. 111-112.
Janz, "Physical activity in epidemiology: moving from questionnaire to objective measurement", Br. J. Sports. Med., 2006, pp. 191-192, vol. 40.
Jia et al., "A food portion size measurement system for image-based dietary assessment", IEEE 35th Annual Northeast Bioengineering Conference, 2009, pp. 1-2.
Jia et al., "Imaged based estimation of food volume using circular referents in dietary assessment.", J Food Eng, 2012, pp. 76-86, vol. 109:1.
Johnson, "MEMS gyro/accelerometer combo chip debuts", EE Times, http://www.eetimes.com/document.asp?doc_id=1257844&armp;print=yes, pp. 1-3.
Justin et al., "Biofuel Cells as a Possible Power Source for Implantable Electronic Devices", IEEE, 2004, pp. 45-46.
Kachigan, "Statistical Analysis: An Interdisciplinary Introduction to Univariate & Multivariate Methods", 1986, Radius Press, New York.
Kaczkowski et al., "Four-Day Multimedia Diet Records Underestimate Energy Needs in Middle-Aged and Elderly Women as determined by Doubly-Labeled Water", J. Nutr., 2000, pp. 802-805, vol. 130.
Karlsson et al., "Considerations on sample size and power calculations in randomized clinical trials", Arthroscopy: The Journal of Arthroscopic & Related Surgery, 2003, pp. 997-999, vol. 19:9.
Kass et al., "Snakes: Active Contour Models", International Journal of Computer Vision, 1988, pp. 321-331.
Kempen et al., "Energy balance during an 8-wk energy-restricted diet with and without exercise in obese women", Am J Clin Nutr, 1995, pp. 722-729, vol. 62.
Kiyokawa et al., "Auditory Detection of Simulated Crackles in Breath Sounds", Chest, 2001, pp. 1886-1892, vol. 119.
Klahn et al., "Temporal and Durational Patterns Associating Respiration and Swallowing", Dysphagia, 1999, pp. 131-138, vol. 14.
Kohl III et al., "Physical Activity and Public Health: The Emergence of a Subdiscipline-Report from the International Congress on Physical Activity and Public Health Apr. 17-21, 2006, Atlanta, Georgia, USA", Journal of Physical Activity and Health, 2006, pp. 344-364, vol. 3.
Kolmogorov et al., "Multi-camera Scene Reconstruction via Graph Cuts", Computer Science Department, pp. 1-16, Ithaca, NY.
Kopelman, "Obesity as a medical problem", Nature, 2000, pp. 635-643, vol. 404.
Lee et al., "DCT-Domain Image Registration Techniques for Compressed Video", IEEE, 2005, pp. 4562-4565.
Levas et al., "The Semantic Analysis Workbench (SAW): Towards a Framework for Knowledge Gathering and Synthesis", IBM Research Report, 2005.

(56) References Cited

OTHER PUBLICATIONS

Lewis, "Power Analysis and Sample Size Determination: Concepts and Software Tools", 2000 Annual Meeting of the Society for Academic Emergency Medicine (SAEM), San Francisco, CA, 2000.

Lhuillier et al., "A Quasi-Dense Approach to Surface Reconstruction from Uncalibrated Images", IEEE Transactions on Pattern Analysis and Machine Intelligence, 2005, pp. 1-16.

Li et al., "Automatic Video Analysis and Motion Estimation for Physical Activity Classification", IEEE, 2010, pp. 1-2.

Li et al., "Chaos-Based Encryption for Digital Images and Videos", Multimedia Security Handbook, Chapter 4, pp. 1-26.

Li et al., "Food density estimation using fuzzy logic inference", IEEE, 2010, pp. 1-2.

Li et al., "Indirect Activity Recognition Using a Target-Mounted Camera", IEEE, 2011, pp. 487-491.

Li et al., "On the Design of Perceptual MPEG-Video Encryption Algorithms", IEEE Transactions on Circuits and Systems for Video Technology, 2007, pp. 214-223, vol. 17:2.

Li et al., "Recognizing Physical Activity from Ego-motion of A Camera", 32rd Annual International Conference of the IEEE, 2010, pp. 5569-5572.

Lichtman et al., "Discrepancy Between Self-Reported and Actual Caloric Intake and Exercise in Obese Subjects", The New England Journal of Medicine, 1992, pp. 1893-1898, vol. 327:2.

Lienhart et al., "An Extended Set of Haar-like Features for Rapid Object Detection", Proceedings of the 2002 International Conference on Image Processing, 2002, pp. 900-903.

Lifson et al., "Theory of use of the turnover rates of body water for measuring energy and material balance", Journal of Theoretical Biology, 1966, pp. 46-74, vol. 12:1.

Liu et al., "An Application of MAP-MRF to Change Detection in Image Sequence Based on Mean Field Theory", EURASIP Journal on Applied Signal Processing, 2005, pp. 1956-1968, vol. 13.

Liu et al., "Automatic Detection of Region of Interest Based on Object Tracking in Neurosurgical Video", Proceedings of the 2005 IEEE Engineering in Medicine and Biology 27th Annual conference, 2005, pp. 6273-6276.

Liu et al., "Automatic Tracking of Region of Interest in Neurosurgical Video", IEEE, 2005, pp. 1-2.

\* cited by examiner

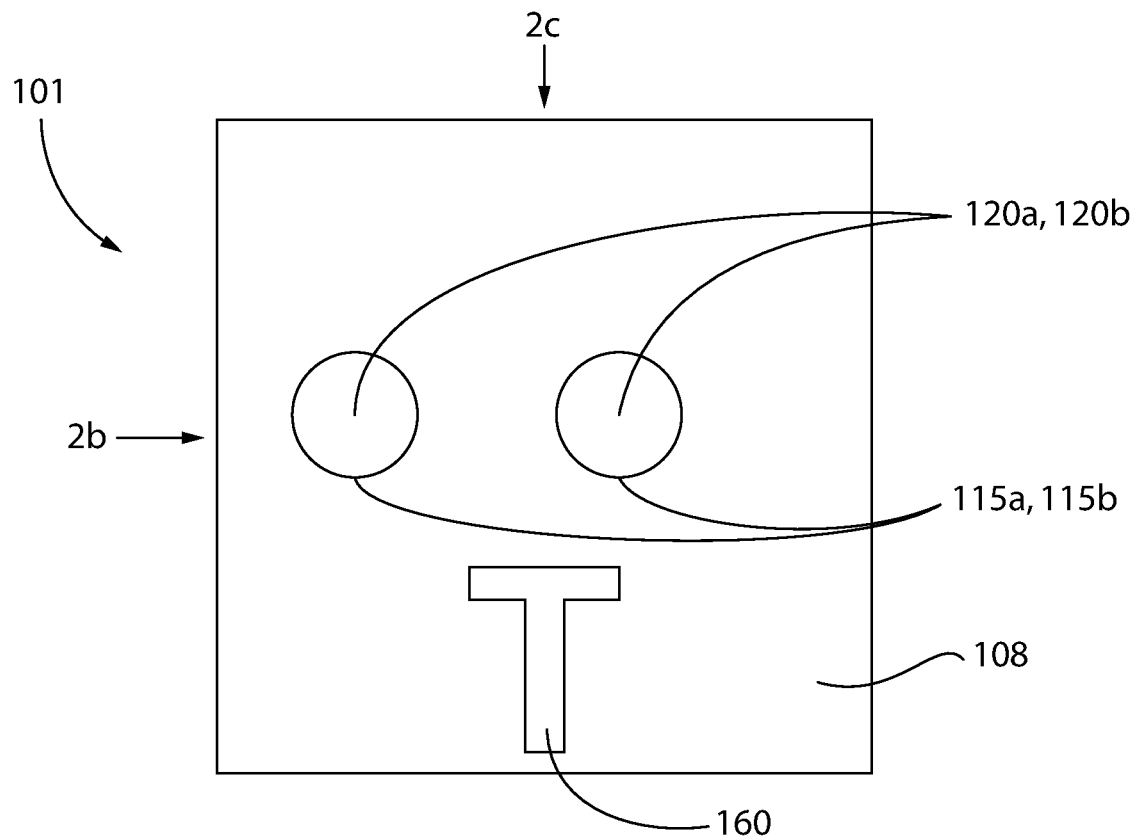
FIG. 2a
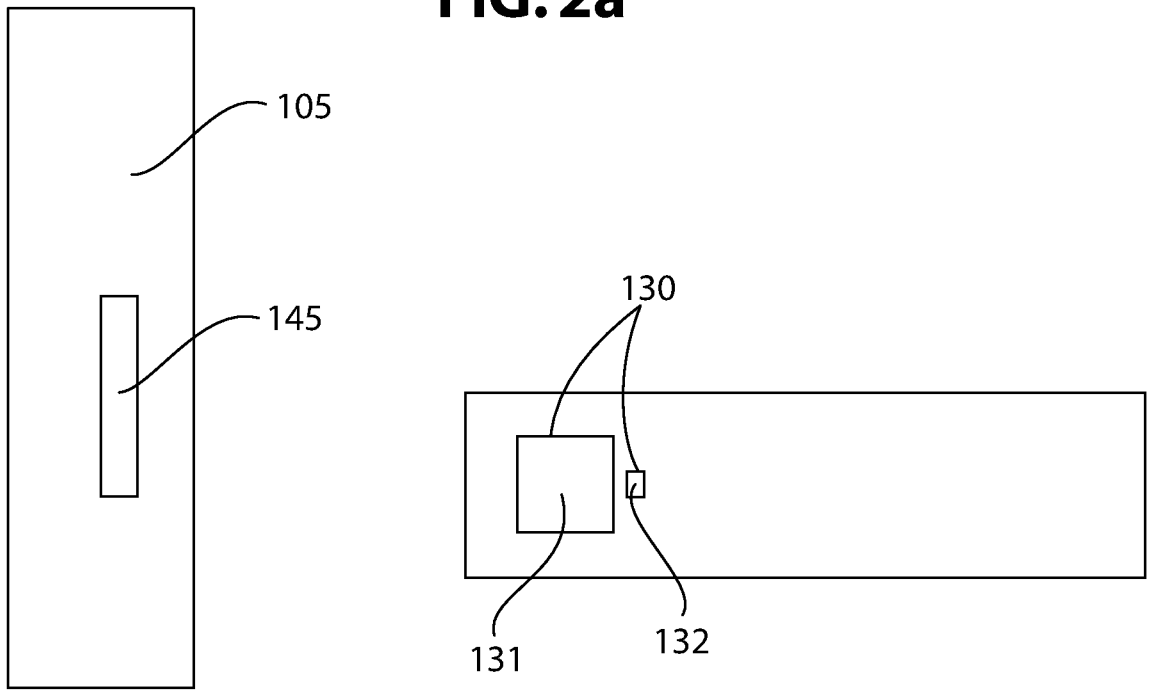
FIG. 2b  FIG. 2c

METHOD, APPARATUS AND SYSTEM FOR FOOD INTAKE AND PHYSICAL ACTIVITY ASSESSMENT

CROSS REFERENCE TO RELATED APPLICATIONS

This application is a continuation of U.S. patent application Ser. No. 13/676,468 filed Nov. 14, 2012, issued as U.S. Pat. No. 10,006,896, which claims the benefit of U.S. Provisional Patent Application No. 61/559,370, filed Nov. 14, 2011, each of which is herein incorporated by reference in its entirety.

STATEMENT REGARDING FEDERALLY SPONSORED RESEARCH

This invention was made with government support under Grant No. U01, HL091736 awarded by the National Institutes of Health. The government has certain rights in the invention.

Provided herein are devices and methods relating to personal monitoring, including without limitation, monitoring food intake and physical activity.

More than 60% of United States adults are overweight, and over one-third are obese. Obesity causes ~300,000 premature deaths each year in the United States A recent study indicates that the estimated direct and indirect costs of obesity to the United States economy are at least $215 billion annually. Obesity is caused by an accumulated surplus of energy, e.g., the calories obtained from foods and beverages exceed those expended on physical activity (physical activity) and metabolic functions. Therefore, measurements of energy intake and expenditure are key to the study of obesity and obesity-linked diseases, such as diabetes, cancer, and cardiovascular disease. Currently, the measurements of food intake and physical activity depend primarily on self-reporting methods. Although such methods of assessment are commonly used in studies, they have clear limitations: results rely on the subject's cognitive ability, memory and willingness to disclose personal behaviors, causing inaccuracy and bias in the measurements. While objective methods have been developed for diet and physical activity assessments, these methods have one or more of the following limitations: labor-intense for human subjects, requiring an institutional setting (e.g., a metabolic kitchen), high cost, and/or questionable accuracy. The research community needs an advanced tool for accurate evaluation of both diet and physical activity in free-living individuals, which would overcome such limitations.

In recent years, some electronic methods have been developed for use in diet evaluation studies. Questionnaires and self-managed diet-evaluation tools can now be completed with an electronic interface or in an internet setting, where digital pictures assist participants in selecting food and determining portion size. A notable development has been the use by participants of a smart phone to take food pictures and transmit them to the laboratory for analysis in real time. Although these methods advance the field of diet evaluation, participants still must play a dominant role in providing diet information, which can disrupt normal eating habits. To avoid this problem, a recent method uses a smart phone worn below the neck (on a lanyard) that records a picture every six seconds and transmits it to the laboratory automatically. However, this method is also limited: the cell phone does not allow long-term operation (relatively short battery life), requiring the subject to turn it on and off frequently (to preserve battery life), thereby disrupting normal behavior around eating episodes.

In sharp contrast to diet, where objective tools are rare, many objective tools are available for physical activity evaluation, such as pedometers, heart rate meters, and accelerometers. However, these tools provide little information about other important factors related to physical activity, such as the subject's behavior and physiological response, as well as built environment (this term refers to man-made surroundings for human activity) and natural environment (e.g., natural landscape, weather, air pollution indices). Some tools are also obtrusive (e.g., calorimetry), costly (e.g., doubly labeled water), suited only to laboratory settings (e.g., metabolic chamber), or inaccurate (e.g., some accelerometers).

In light of the deficiencies of currently available methods and devices for dietary and physical activity analysis, there is a need for a device which is: 1) objective regarding diet and physical activity data collection, 2) low-cost, 3) unobtrusive, 4) a low burden on participants, 5) cosmetically appealing, and 6) multi-functional. Furthermore, there is a need for a device that provides not only data for energy intake and expenditure calculations, but also information about built/natural environment, behavior, and physiological responses of a subject. Lastly, there is a need for a device that accurately and automatically identifies eating and physical activities and that can automatically catalog food items with minimal user input.

SUMMARY

Electronic systems, devices and methods are provided to accurately measure both food intake and physical activity. A novel multimedia method, an electronic device, and an integrated data processing system are described. Methods of use of the device also are described.

A device is provided for the remote monitoring of food intake and physical activity in a subject. According to one embodiment, the device comprises a housing; a power supply; and in the housing: one or more physiological sensors; two or more video cameras positioned in the housing to produce stereo images which, when viewed together, create a three dimensional perspective; a data storage device; and one or more processors (e.g. microprocessors) connected to the physiological sensors, one or more cameras for both images and videos, the data storage device and the power supply. The microprocessor(s) manage the collection, storage, and transmission of data from the physiological sensors and the video cameras, and other optional components configures within the device. In order to function, the device comprises a program that controls data acquisition from the video cameras and one or more physiological sensors and data storage on the data storage device, and optionally data analysis and conversion. The elements of the device are connected by and the effects of the device are implemented by suitable electrical or electronic elements, (e.g., terminals and connectors, wires, conductive traces, resistors, capacitors, transistors, integrated circuit chips, switches, diodes, protective devices, inductive devices, piezoelectric devices, crystals, resonators, etc).

In one non-limiting embodiment, the data storage medium is a flash-type memory card such as a MicroSD card or a USB thumb drive for recording data. The card or drive is removable so that recorded data can be transferred to a computer or other external device.

In addition to a data recorder, optionally, the device further comprises a data transmission interface connected to the microprocessor(s) and/or data storage device which transfers data from the sensors, processors or data storage device to and/or from an external device. The transmission interface comprises either a wireless data interface, e.g., a transmitter, receiver and/or adaptor such as a Bluetooth, WiFi, cellular network or infrared interface or a hard-wire connection such as Universal Serial Bus (USB) connector. The power supply, for example a battery, is located either within or external of the housing.

Non-limiting examples of the one or more sensors of the device include an accelerometer (two-dimensional (2D) or three-dimensional (3D)), a gyroscope (2D or 3D), an indoor/outdoor detector, a temperature sensor, an audio system, an eating detector, an oxygen saturation sensor such as an ear-based oximeter, and an electrode system. According to one embodiment, the eating detector is an optical eating detector that projects a light beam in the region in front of the mouth of the subject and measures when an object, such as a food item, passes through the region. Examples of light beams include an infrared light beam, a laser beam, or a beam of light omitted by a light emitting diode (LED).

In one embodiment, the device further comprises one or more geographical and environmental sensors. Non-limiting examples of these sensors include a global positioning system (GPS) sensor, an ultra violet (UV) radiation sensor, a thermometer, and a humidity sensor.

The device optionally further comprises one or more indicia and/or aesthetic features. The indicia or aesthetic features are adaptable for the tastes of individual subjects. An exemplary aesthetic feature for such an embodiment of the device is a logo of a favorite team, university, or other entity with which the subject is affiliated. The aesthetic feature typically is on an outward-facing surface of the device.

In one non-limiting embodiment, the device is adapted to be worn as a button wherein the housing comprises a shell, such as a cylindrical shell, which contains the electronic components, including visual, geographical, motion, orientation, and/or environmental sensors, two video cameras in a stereoscopic arrangement, a recording device, and a power supply. Optionally, a lead (e.g., a wire) attached to the device connects the device to an ear-based oximeter for measuring oxygen saturation and/or electrodes to measure physiological variables, such as the heart rate and the respiration rate.

According to another embodiment, a system is provided for remote monitoring of food intake and physical activity in a subject. In one example, the system comprises: a device for monitoring food intake and physical activity of a subject and a computer. Optionally, the computer has a reader for receiving data from the device and inputting the data into the computer for processing. The reader is one or more of a card reader for receiving a data storage card from the device, a wireless data link comprising the following sensors in separate chips or a combined chip such as a Bluetooth network chip, a Wi-Fi chip, a service-activated cellular network chip, and a GPS receiver. According to one non-limiting embodiment, the wired information link consists of a hardwired connection such as a USB port. In one embodiment, the system comprises one or more computer programs for determining a dimension of a food item in video data obtained from the video cameras and for determining a physical activity of a subject wearing the device. In one example of the system, the program for determining the dimension of a food item from video data obtained with the video camera is a food model fitting type analysis using a stereo image from the two video cameras. Similarly, the program for determining physical activity of the subject wearing the device is an automated process using an algorithm performed by a computer or a manual review process.

In another embodiment, a method is provided for remote monitoring of food intake and physical activity in a subject. In one example, the method comprises obtaining video data in the form of a stereo image from two or more video cameras suitably placed on a subject to show food consumption by the subject and physical activity of the subject; and determining from the video data one or both of food consumption by the subject and physical activity of the subject. The method optionally comprises limiting times when data regarding food intake is recorded to times when the subject is eating by using an optical eating detector to determine when eating occurs. The method also optionally comprises altering the frame rate and resolution of the cameras as well as turning one or both of the cameras off at times when the subject is not eating or is sedentary as detected by the accelerometer and/or gyroscope. The cameras can also be controlled selectively at different geographic locations (determined by the GPS sensor and/or indoor/outdoor sensor).

Also provided in the present application are methods of monitoring behavior, condition or activity of a subject. Such parameters may be monitored by recording output of a device comprising one or more sensors such as without limitation oximeters, heart rate monitors, accelerometers, and gyroscopes. The sensors may also include environmental sensors such as GPS sensors, magnetometers, electronic compasses, thermometers, VOC sensors, ambient sound recorders, humidity sensors, and UV sensors, two or more imaging sensors, and an eating detector. The device may held in a housing and may include a bus, a microprocessor connected to the bus, and a data storage device including data storage medium and a program for managing data acquisition and storage. The device also includes a power supply.

In non-limiting embodiments, the method may be used to collect information on behavioral, condition or activity data for specific populations. For example and without limitation, the methods may be used to collect information from police officers, astronauts, or consumers in a shopping environment (e.g. in a particular store or mall). The method may also be used to assess the behavior, condition or activity of animals, for example livestock on a farm or grazing on grazing lands.

BRIEF DESCRIPTION OF THE DRAWING

The figures are provided for illustrative purposes only and are not intended to limit the scope of the present inventions.

FIGS. 1a, 1b and 1c show top and two side views, respectively of the device. FIG. 1D depicts a cross section of the device.

FIGS. 2a-2c depict schematically a second embodiment of the device for monitoring of food intake and physical activity in a subject

DETAILED DESCRIPTION

Figure 1A:
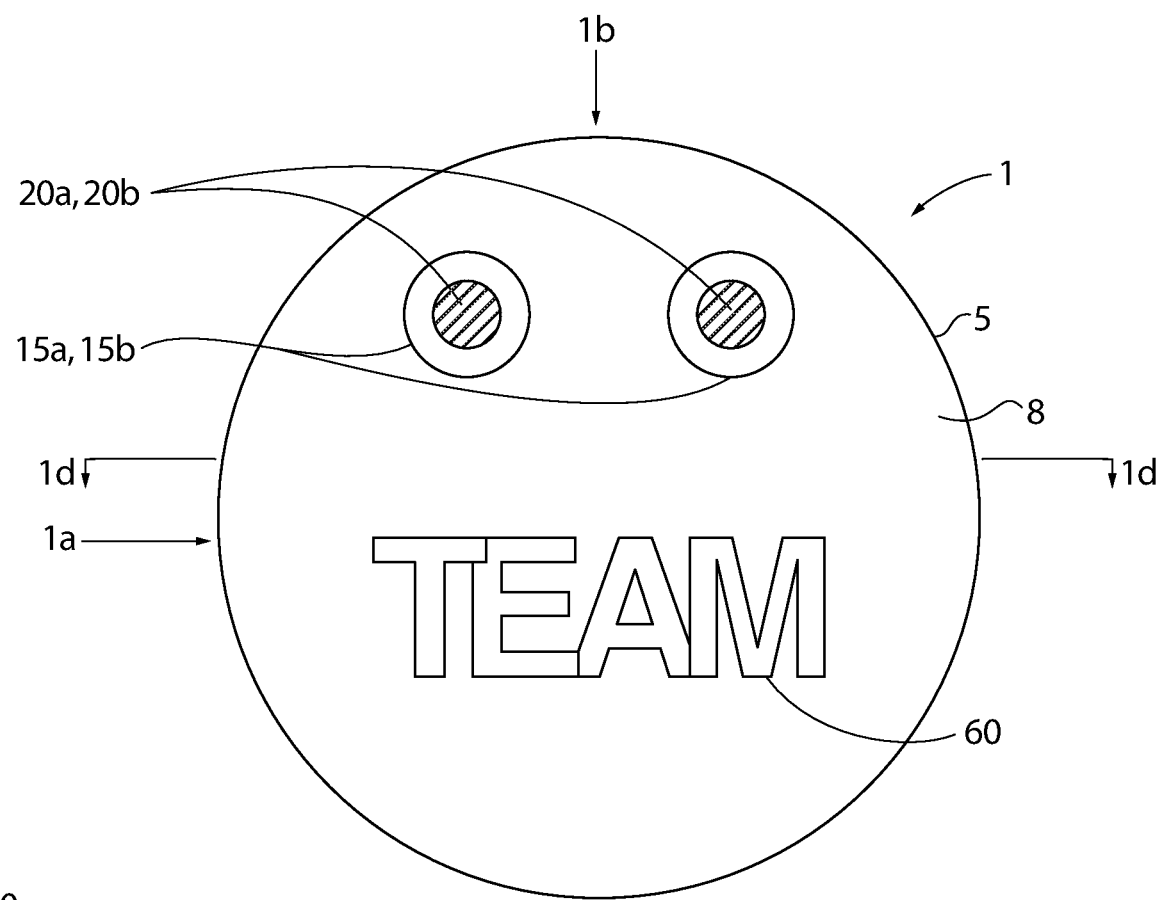
FIGS. 1a-1d depict schematically one non-limiting embodiment of the device for remote monitoring of food intake and physical activity in a subject.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the term "patient" refers to members of the animal kingdom, including but not limited to human beings, and implies no relationship between a doctor or veterinarian and a patient.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps. "A" or "an" refers to one or more.

A device is provided for monitoring food intake and physical activity in a subject, which includes monitoring the physical surroundings of the subject as well as physiological parameters and activities of the subject. In one embodiment, the subject is a patient, e.g., an obese patient or a patient suffering from diabetes, seeking to collect objective data regarding eating habits and physical activity for treatment. Patients suffering from other chronic diseases whose effects are exacerbated by environmental factors may also use the device to collect objective data about diet, environmental conditions, and physical activity relevant for their treatment and condition. In another embodiment, the device assists blind persons in moving around by tracking location and alerting the user of objects in their path. In another embodiment, individuals, especially senior citizens, wear the device as a personal safety device to signal for help in the case of physical trauma (e.g., heart attack, stroke, traumatic physical injuries). In other embodiments, the subject is an athlete collecting data to assist in creating a physical training and nutrition regimen; and employees, so that the employer can collect data regarding physical demands of a job, active duty police officers and military, or astronauts during space missions. Similarly, the subject could be a shopper or consumer, allowing the store to collect data about shopper habits. In another embodiment of the device, a subject is a wild animal. For example, ecologists or biologists may use the device to collect data to better understand eating habits, responses to environmental stimuli, and physical activity of animals in the wild.

In a most general sense, the device comprises a housing. The housing is manufactured from any suitable material or combination of materials, including, for example: plastic ((co)polymer(s)), glass, ceramic, or metal. The housing comprises an interior cavity. The housing optionally includes one or more indicia and/or aesthetic features, such as a decal depicting a sports team's logo, affixed to an outer surface of the housing, such as an outward-facing surface of the housing. Any element of the device that is contained wholly or partially within the housing, such as a battery within the housing or a lens protruding through a hole in the housing, are considered to be "in the housing". The device comprises two or more imaging sensors, such as cameras or video cameras, arranged for stereoscopic imaging, a data storage device, a power supply, and, optionally, other types of sensors, such as: an eating detector (e.g., for determining when the subject is eating and for controlling the collection of data with regard to eating habits), an accelerometer (e.g., for measuring body acceleration), a gyroscope (e.g., for measuring body orientation), a GPS sensor (e.g., for determining the subject's geographical location), an oxygen saturation sensor (e.g., for measuring blood oxygen level and/or heart rate), an electrode (e.g., for measuring for skin impedance) and an audio sensor/player (e.g., one or both of a microphone and a speaker or a plug/adaptor for a speaker or amplifier/speaker combination). Suitable sensors capable of being adapted for use with the device are available from a variety of commercial sources.

The components of the device, such as cameras/imaging sensors and sensors are combined in various manners with various analog and digital circuitry, including controllers, filters, ADCs (analog-digital chips), memory, communication devices and adaptors. As devices become smaller and processors become more powerful and use less energy, it is possible to integrate many more sensors, such as NEMS (microelectromechanical or nanoelectromechanical systems), onto single chips. MEMS accelerometers, gyroscopes, gas sensors, thermomoeters, humidity sensors, magnetometers, etc. are readily available from commercial sources and/or are abundantly described in the art. Technologies such as package on package (PoP) and system on a chip (SoC) integrated circuit packages allow manufacture of very small devices with significant capacities. For example, smart phones use PoP technologies to stack memory and processors in a very small volume. One example of a SoC is a microcontroller (MCU), which is a small computer on a single integrated circuit typically containing a processor core, memory, and programmable input/output peripherals. Microcontrollers also may include timer module(s) and analog-to-digital converter(s) for, e.g., converting analog sensor output to a digital signal. High definition video cameras are available that measure less than 10 mm on a side. For example, a prototype device having eight PCB layers, an ARM 11 microprocessor, 32 GB (gigabytes) of flash memory, a video camera, a multi-axis accelerometer, a daylight sensor, a thermometer, a digital compass, an ambient sound recorder and a lithium ion battery was manufactured into a circular disc (pin) that is 61 mm in diameter, 10 mm thick, and weighs 40 g.

A "bus" is a subsystem that transfers electrical signals, e.g., data, between components inside a computer, or in the present instance within the device and often is a PCB, but can be any connector capable of transferring electrical signals between components of the devices described herein, including connections or connection points in PoP and SoC structures. Further, by a stated component being "connected to the/a bus" it is meant that component is electrically connected to the bus and in functional electrical communication (including data communication as is applicable) with other components of a device connected to the bus according to the design of the device.

An accelerometer measures acceleration. Most accelerometers can also measure tilt. The accelerometer was originally a large device, but with the continued advances in the field of micro-electromechanical systems (MEMS) technology, they now are available in sizes as small as 2.9×2.9×0.92 mm with 3-axis measurements. The architecture of the MEMS device initially used a suspended cantilever beam. Recently, a newer architecture has been developed using a heated gas bubble with thermal sensors. When the accelerometer is tilted or accelerated, the location of the gas bubble causes variations in the output. Although most applications of accelerometers are found in the automobile industry, such MEMS devices also are useful in biomedical applications, such as in physical activity, swallowing, and respiratory measurements. Although other types of accelerometers may find use in the devices described herein, a 3-axis accelerometer may be preferred in most instances for characterization of physical activity.

A gyroscope measures orientation. In one embodiment of the device, a gyroscope is used to determine changes in the orientation of the subjects' body to help identify the physical activity performed. A mechanical gyroscope was originally a large device consisting of a rotor mounted within a frame structure of concentric circular members. The device measures changes in angular momentum. Gyroscopes based on MEMS technology are now widely commercially available. Available MEMS devices use one or more mechanisms for measuring orientation including tuning forks, vibrating wheels, or resonant solids of various designs. Major manufacturers of gyroscope chips are Panasonic, Robert Bosch GmbH, Seiko Epson, STMicroelectronics, and Analog Devices. Commercially available products have dimensions of about 4×4×1 mm. Commercial chips that combine a 3-axis accelerometer and a 3-axis gyroscope within one package are now available.

An oxygen saturation sensor indirectly measures oxygen saturation of arterial blood. For example, a pulse oximeter is a medical device that indirectly measures oxygen saturation by passing light in the red or infrared wavelengths through the skin of a subject and measuring the change in absorbance due to pulsing arterial blood. In one embodiment, the oximeter is an ear-based oximeter having a lead extending from the device housing to the ear of the subject. Commercially available ear-based oximeters adaptable for use with the present device include the BCI ear sensor clip for the BCI 3301 oximeter, the Nonin PureLight ear clip sensor manufactured by Nonin Medical, Inc., Plymouth, Minn., the ChipOX SPO2 Pulse Oximeter Module, and various ear sensor clips manufactured by ENVITEC-Wismar GmbH, Wismar, Germany. Ear-based oximeters may either attach to the ear lobe (so as not to impede hearing) or be inserted directly to the ear canal. Currently available oximeters measure both heart rate and oxygen saturation ($SaO_2$). A newer enhanced ear-based oximeter is expected to become commercially available which also measures maximal oxygen consumption ($VO_2$). It is anticipated that the enhanced sensor may also be adapted to work with the device.

The imaging sensors, for instance a camera or video camera, may be any useful device for generating and subsequently recording useful image data. Although designs from different vendors are different, a video camera usually consists of a charge-coupled device (CCD) or complementary metal-oxide-semiconductor (CMOS) imaging sensor, a lens, a multifunctional video control/DSP chip, and a set of discrete components (e.g., capacitor, resistors, and connectors). The lenses either have a focus range useful for imaging as described herein or they comprise an auto-focus feature. Likewise, the lenses may be equipped with a zoom functionality. While the video control component on the chip performs a number of image acquisition tasks, the DSP component on the same chip implements data processing algorithms, such as noise reduction and simple forms of data compression and encryption. The digital output from the video control/DSP chip may be in either a parallel or a serial form, depending on the particular chip design and the input configuration in the next data processing or interface stage.

In one example, the imaging sensor is a video camera device manufactured by Sanyo Electric Co., Ltd., Tokyo, Japan (Part No. IGT99267J-ST). The size of the module is less than about a half an inch in its longest axis. Its size is adequately small for the devices described herein. The lens is an auto-focus camera lens that can be selected for its focal length. Choice of focal length represents a design element and is optional. A shorter focal length is helpful in terms of privacy protection, as only images within a certain proximity of the camera and the individual will be seen clearly. Beyond this focal distance, images would appear more blurred and perhaps indistinguishable, which would be desirable, for instance, with respect to preventing individuals from being identified with whom the subject volunteer comes into contact. The video camera also comprises a video control/DSP chip, a number of passive components, a printed circuit board (PCB), and a flexible wire strip including a connector for data and power transfer. This particular camera can record 354×288 color video (a resolution comparable to that of a VHS video tape) at 15 frames per second with a peak power consumption of 45 mW. Besides this device, newer commercial chips (e.g., part number OV6130-C00A, available from OmniVision, Sunnyvale, Calif.) with comparable resolution exist, but are smaller in size and demonstrate lower power consumption (<20 mA when active). Higher-end chips supporting much higher resolution (e.g., DVD resolution or higher) and frame rates (≥30 fps) also exist that are equipped with sophisticated imaging control and programming functions. However, these are achieved at the expense of higher power consumption. In configuring the systems described herein, factors such as the total power consumption of the device (which preferably is less than 50 mW (on average) for a one-day (12-18 hours) operation), video quality, complexity in circuit design, and the available space will have to be considered. At such low-level power consumption, the heat generated by the device should be negligible.

Aside from its usefulness in producing images that can be analyzed as described herein for food intake and activity assessment, the stereoscopic nature of the imaging system serves the purpose of rangefinding and sizing of imaged items such as food items. In an earlier system described in US-2009-0012433-A1, a laser rangefinder is used to automatically identify distances so that the size of food items might be calculated. This is not only obtrusive, but requires an entirely separate electronic subsystem in the device, and separate software implementations. Also described in that publication is use of a reference item that is inserted in the image of the food—requiring the user to carry the reference item and display it every time food is used. This, too, is cumbersome, and adds an additional level of complexity to the end-use of the device. To the contrary, stereoscopic imaging requires no user input, reference cards or obtrusive laser beams.

Imaging sensors, such as video cameras or cameras, can be said to be positioned (e.g., in a housing) to record a stereo image pair or to record a stereo image. This means that the cameras, typically two cameras, are arranged and positioned in the housing so that images produced by the cameras are able to produce a three-dimensional, stereoscopic image. A stereoscopic image creates the illusion of depth (three dimensions) by presenting the two offset images separately, e.g., to the left and right eye of a viewer or to a computer viewing/analysis program. Based on the three dimensional image, as shown below, it is possible to accurately estimate dimensional data including the actual distance from the camera and dimensions of objects depicted in the image. Dimensional estimates from stereo images are obtained without using reference cards or reference objects to estimate size and distance—a substantial advance over prior methods. In the context of the devices, systems and methods described herein, so long as there is sufficient distance between the imaging sensors and their field of view overlaps in a useful distance range for creating a stereoscopic image that is useful for the function of the device (for example and without limitation, from 1 to 20 feet and any range therebetween), the cameras are considered to meet this criteria.

A stereoscopic image is considered to be and can be referred to as a "representation of a stereo image" in certain instances in recognition that programs can vary widely in how they utilize output data from the stereo-arranged cameras to achieve a particular operation goal, and may not generate a stereo image per se as part of the process, but some representation of that image pair that can be evaluated by a computer program to achieve a desired programming goal—irrespective of whether a stereoscopic image that is viewable by an individual is actually generated. For example, stereo images will greatly improve the system's ability in food portion size measurement. Currently, a reference object (e.g., a checkerboard) must be present within the food image. With the stereo imaging system, this limitation can be removed since the distance between the two cameras can then be used as a reference. Stereo images are also essential in many other applications, such as navigation for the visually impaired persons. In this case, the distances of obstacles can be computationally estimated from such images. In one non-limiting embodiment, the imaging sensor is a video camera is capable of recording images at a variable frame rate from at least 30 images per second to as low as 0.1 frame per second. A stereoscopic image pair is a pair of images that can be viewed together to form a stereoscopic image.

In the most general sense, the device further comprises a data storage device. In one non-limiting embodiment, the data storage device is a digital data recorder such as a disk drive which records data onto a data storage medium. In another embodiment, the data storage medium is flash memory. The data storage medium is any type of non-volatile memory, for example, magnetic data storage media such as a hard disk drive or magnetic tape, or flash-based memory. Flash memory is a non-volatile computer storage chip using NAND or NOR type memory as found in MicroSD cards, USB flash drives, or solid-state drives. File systems optimized for flash memory (solid state media) include Embedded Transactional File System (ETFS), exFat and FFS2 systems. The data storage medium can be random access memory (RAM) or read only memory (ROM). The memory may be removable from the device or permanently installed within the housing and transferable to an external device through the data transmission interface.

In one embodiment, the device further comprises one or more power supplies such as a battery. A battery comprises one or more electrochemical cells that convert stored chemical energy into electrical energy. One non-limiting example of a useful battery is a lithium-ion battery. A lithium-ion battery is a rechargeable battery often used in electronic devices. It is preferable that the capacity of the lithium-ion battery provides enough power for the device to operate continuously for 15-16 hours (entire daytime). In some cases where the device is not operated continuously, however, a battery of smaller capacity is more appropriate for reduced device size and weight. Other types of batteries, adaptable for us in the device include nickel cadmium (NiCd), and nickel medal hydride (NiMH) batteries. Preferably the battery is rechargeable and, in that case, the device further comprises a battery recharge port.

The device described herein is controlled by one or more single-core and/or multiple-core microprocessors, essentially turning the device into a wearable computer. A microprocessor is a chip containing one or more integrated circuits which receives data and processes the data according to instructions stored in the chip's memory. A microprocessor typically, and along with other functions, manages the collection of data from the various sensors and the video cameras, directs the storing of data by the data storage system and typically allocates system resources between the electronic components to reduce power consumption and decrease the need for duplicative electronic systems. One type of microprocessor which can be adapted for use with the present device is an ARM Cortex 9 processor running a simplified UNIX operating system. This type of processor is commercially available from numerous sources. In order to save power and allow for parallel data processing, MCUs, which consume much less power than the main processor, can be used when the computing demand is low (the main processor can be powered down), and when the computing demand is high (all processors are activated). This multi-processor strategy is similar to the case of the hybrid car in which two types of engines are used to meet different power demands.

As mentioned above, one sensor optionally included with the device is an eating sensor. The eating sensor is used to determine when the subject eats and to ensure that eating events are recorded for later analysis. Based on the data collected, information including portion size, nutritional value, and caloric intake is determined. Previous eating detectors relied on an accelerometer physically and intimately attached to the subject (e.g., attached to the jugular notch of the subject using an adhesive) to determine when the subject swallowed. Attaching a device to the subject is not optimal. According to one embodiment of the device described herein, the eating detector is an optical detector comprising a diode, which projects a beam of light, such as infrared light, or a laser beam, to a region in front of the mouth of the subject, and a position detector. The beam of light may be distributed in a fan shape, creating a trapezoidal detection zone in front of the mouth of the subject. The position detector comprises a photodetector, such as a sensitive phototransistor. The photodetector and associated circuitry measure changes in light or radiation intensity, thereby determining when an object passes through the mouth region. Light emitting diodes and photosensors, such as phototransistors, are commercially available from numerous sources including Sharp, Inc. In use, an object passes through the detection area when the patient eats, drinks, or smokes. The detector optionally uses a processing algorithm, typically in conjunction with the microprocessor, to distinguish false positives such as when a subject yawns or touches her face as opposed to actual eating events. According to one embodiment, when the sensor determines that the subject is eating, a signal is sent to the video cameras to signal the cameras to record at a high frame rate and high resolution to ensure that the eating event is adequately recorded. At other times, such as when the subject is engaged in sedentary activity as detected by the accelerometer (e.g., watching TV), only a single camera records at a reduced frame rate. In this way, the eating detector regulates power consumption, reduces the amount of redundant data, and conserves storage capacity.

In addition to the sensors described above, adapted to measure physiological factors, additional embodiments of the invention include one or more environmental sensors to record information about the subject's surroundings. Non-limiting examples of environmental monitoring sensors include: a global positioning or Global Positioning System (GPS) sensor (e.g., for determining and recording the subject's location), an ultraviolet (UV) light sensor (e.g., for measuring whether the subject is indoors or outdoors and for measuring exposure to sun radiation), a thermometer and a humidity sensor. In one embodiment of the invention, location data obtained from the GPS is used in combination with environmental data obtained from a public database, such as the air quality database maintained by the United States Environmental Protection Agency (EPA). The EPA database includes environmental information collected from a dense network of monitoring stations located throughout the country. Measurements relevant to the analysis of physical activity and well being include measurements of: weather condition, atmospheric particulates (e.g., PM2.5), carcinogenic particles, allergens, toxins and ozone. Optionally, an algorithm is used to estimate environmental conditions at the subject's exact location by extrapolating, interpolating, differencing, etc. conditions at two or more nearby or nearest monitoring stations to, e.g., account for other environmental factors, such as wind strength and directions. In one embodiment, data is downloaded to the device using the data transfer interface for real-time comparison and monitoring. An example of such a database is the EPA's Air Quality System (AQS) Data Mart. Information on this database is available at http://www.epa.gov/ttn/airs/aqsdatamart/index.htm.

In one embodiment of the device or system described herein, the device further comprises a data transmission interface for sending and receiving data to and from external sources, in effect, creating a personal area network (PAN) comprising the device, the data transmitter and an external receiver attached to an external source. A PAN is a computer network used for communication (e.g., data transmission) among computer devices including telephones and personal digital assistants (PDAs) in close proximity to the user's body. PANs can be used for communication among the personal devices themselves (intrapersonal communication), or for connecting to a higher level network and the Internet (an uplink). Networks may be wired, using, e.g., USB, ethernet and FireWire protocols. A wireless personal area network (WPAN) is made possible with wireless network technologies such as Bluetooth, WiFi, Z-Wave and ZigBee. WiFi (e.g., IEEE 802.11a, b, g, n) networking protocols may be used, which advantageously have a greater transmission range than (e.g.) Bluetooth, but consequently also have greater power consumption. Suitable external sources for receiving data transmitted from the device and optionally processing the data include a computer, tablet PC, or smart phone and/or an external hard drive or other device for backing up stored data.

The device optionally comprises one or more privacy features. In one embodiment, data within the device and/or transmitted to and from the device is protected by encryption, according to any useful method. Privacy of the subject wearing the device or others can be protected by hardware or software components that allow for turning off recording from one or more of the cameras or when present a microphone, at any time when privacy issues are raised by recordation of data by the device, for instance at times when the subject is at the work site (as determined by the GPS sensor), being sedentary (as determined by the motion sensors), or anywhere either indoor or outdoor (as determined by the ultraviolet light sensor), etc. In addition, according to one embodiment, the frame rate of the video recording is reduced at times which the cameras are unlikely to record relevant data so that personal identifying information is not recorded. Additional privacy measures include face-recognition and obliteration programs that automatically recognize human faces and blur them or otherwise prevent recognition.

In another embodiment, efforts are taken to ensure that the privacy of the subject is protected as the data obtained by the device is analyzed. Multi-layered protection may be utilized to guard against any possible failures to preserve privacy of both the subject and any bystanders. Each security layer is independent and, consequently the device, may include all, some or none of these layers. For example, a first security layer may involve installing hardware on the device specially designed electronic components to limit the scope (depth of field) of the video camera. A second security layer may use advanced encryption of all multimedia data. In one embodiment of the privacy protocol, no human is allowed to access any information during data recording, transmission, and transportation. A third security layer may comprise extensive filtering implemented by software. For example, all images of humans appearing in the entire video record may be automatically identified and destroyed. Again, no human needs to be involved in this security layer. In a further example of a security layer, passwords are used to allow authorized persons (e.g., who are called "honest brokers" as defined by HIPAA US Federal privacy regulation), who are required to sign a legal document of non-disclosure, to access data stored on the device. This access is possible only after all the previous security layers are automatically implemented. In an additional layer of privacy protection, a convenient mechanism can be provided by the systems to switch-off or block the camera in sensitive locations or public places where photographing or video-taking is prohibited.

The device comprises computer one or more programs (e.g., computer programs) for implementation of the functionality of the device. As used herein and as described in further detail below, a "program" comprises processes, modules, routines, subroutines, algorithms, software, executable instructions, etc. for implementing an action in a computer, such as a microprocessor-based device as described above. This is achieved by processing executable instructions by a processor.

In another non-limiting embodiment, a system is provided for remote monitoring of food intake and physical activity in a subject. A system refers to a combination of elements including a device for the remote collection of food intake and physical activity data as described herein and a computer for running programs, processes, algorithms, etc. such as programs for classifying, analyzing, modifying, converting and/or organizing the data. A computer can be any device for processing data including a smart phone, tablet PC, calculator, or standard laptop or desktop computer. A computer program is software that implements a certain specified function in the device, and can include algorithms or other structural features, and which can work with hardware in implementation of the certain task. A process is an active implementation of a program or a portion of a program. For instance, a "program for facial recognition and obliteration" is a program (e.g., software) that resides in the device and which has the capacity to recognize a face in a video image data and render the face unrecognizable in one or more images stored on the device that include the face. Programs for implementation of specified tasks are typically readily developed by one of ordinary skill in the art and can take a variety of physical/logical forms. Programs are stored on any useful data storage device (e.g., ROM or other non-volatile memory) as are broadly known in the computer arts. A database is an organized collection of data typically stored in digital form. A system may comprise a database, with includes either a local database stored on data storage medium in the computer and/or the device or an active or activatable link providing access to data in a remote, e.g., public, database such that information required for activity of the program is obtained by remote connection to the remote database.

The system comprises a communications interface which receives data from the device and inputs the data into the computer. In another embodiment, the communications interface is a card reader such as a flash memory or MicroSD disk drive which receives a removable storage disk from the device and transfers the recorded data to the computer. In other instances, the communications interface is a wireless receiver such as a Bluetooth network card.

Dimension of food item: In one embodiment, the system includes a program for determining dimensions of a food item. The computer program includes function(s), e.g., algorithms, that identify food dimensions according to a form fitting model that estimates food volume from images recorded by the video cameras. As an example, a pair of stereo images, such as the images recorded by the two or more video cameras of the device, can only reconstruct a portion of the 3D food surface. Fortunately, most human foods have roughly known geometries (e.g., a piece of pizza is roughly a triangular prism). Therefore, food item volume can be estimated even when only part of the 3D surface is observable. An exemplary form fitting algorithm operates according to a virtual reality (VR) method wherein a computer-generated template is scaled, rotated, and deformed to virtually fit the food, as shown in the recorded stereo image, in the virtual image space in FIG. 7. The template is fit to the image of the food item using a least-square fit algorithm. When the camera is well calibrated, a wireframe virtual template provides an accurate measure of the portion size.

Determining physical activity: Where physical activity of a subject is determined, data is recorded as the subject engages in physical activity; the data is later reviewed either manually or by an automated process using a computer to identify and classify the physical activity performed by the subject. In an example of a manual method for determining physical activity, screenshots are viewed directly by a data assistant. The data assistant prepares an event summary package using software developed for that purpose. Using the software, the assistant reviews each screen shot utilizing an extremely fast "multi-touch" interface to review and label screenshots in quick succession. The assistant optionally also combines physical activity, diet, and behavior information into the event summary package.

In other embodiments, physical activity is determined by an automated process using computational algorithms. In one example of a method utilizing an automated process for identifying physical activity, a modeling computer program is used to simplify activity classification. According to one embodiment, numerous potential physical activities are decomposed so as to define a set of Eigen activities. Eigen activities are much easier to classify by the computer compared to the innumerable physical activities which could be performed by a subject. The Eigen value concept is parallel to a powerful mathematical concept where a large number of functions can be approximated using a much smaller set of basic functions. Briefly, the data is first broken down using an improved version of a segmentation algorithm. Then, the measured physical activity data within each "screenshot" is pre-processed individually to extract "features". Next, a classifier is used to classify the feature vectors into Eigen activities (EAs). This EA sequence is then analyzed by the second classifier that determines physical activity based on a hidden Markov model or a linguistic model. Under a hidden Markov model, a given series of observations (data from the video camera and other sensors) is used as an input, and according to the algorithm, the most likely corresponding sequence of states (the Eigen activity) is computed. In addition to using video data to identify physical activity, data from the other sensors may also be relied upon to further distinguish and classify various physical activities. For example, the accelerometer identifies trunk acceleration, the gyroscope indicates trunk orientation, the GPS identifies physical location (near buildings or in an outdoor environment), the oximeter evaluates heart rate and $O_2$ saturation, and the UV sensors to indicate whether the subject is indoors or outdoors. In certain non-limiting embodiments, recording of data by the system is triggered by thresholds that are detectable by one or more of the sensors. For example and without limitation, recording may be triggered by movement of the subject at a certain threshold speed (i.e. indicative of walking, cycling or running) for a set period of time (i.e. for at least 30 seconds, 15 seconds, or 5 seconds).

Figure 1B:
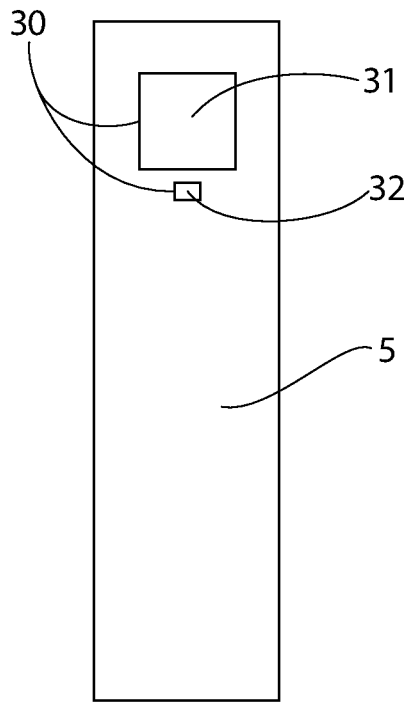
Figure 1C:
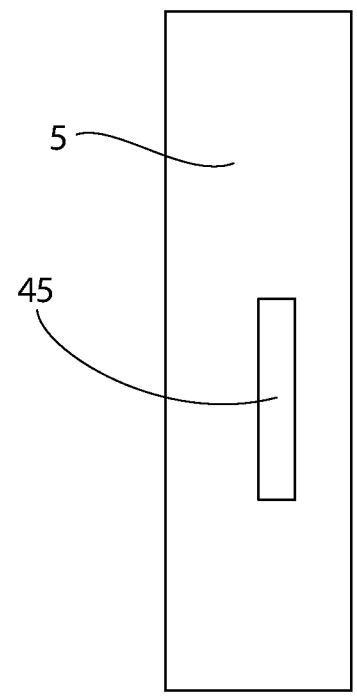
Figure 1D:
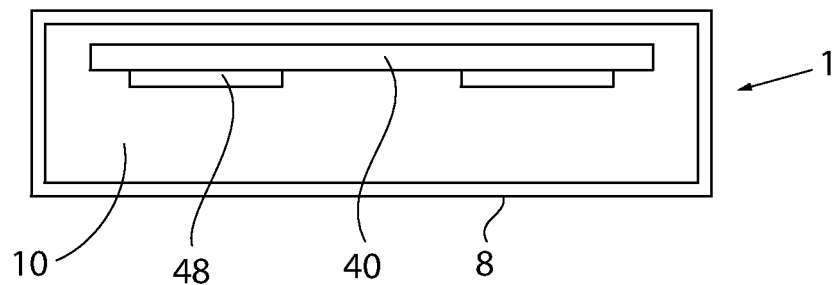
Figure 1E:
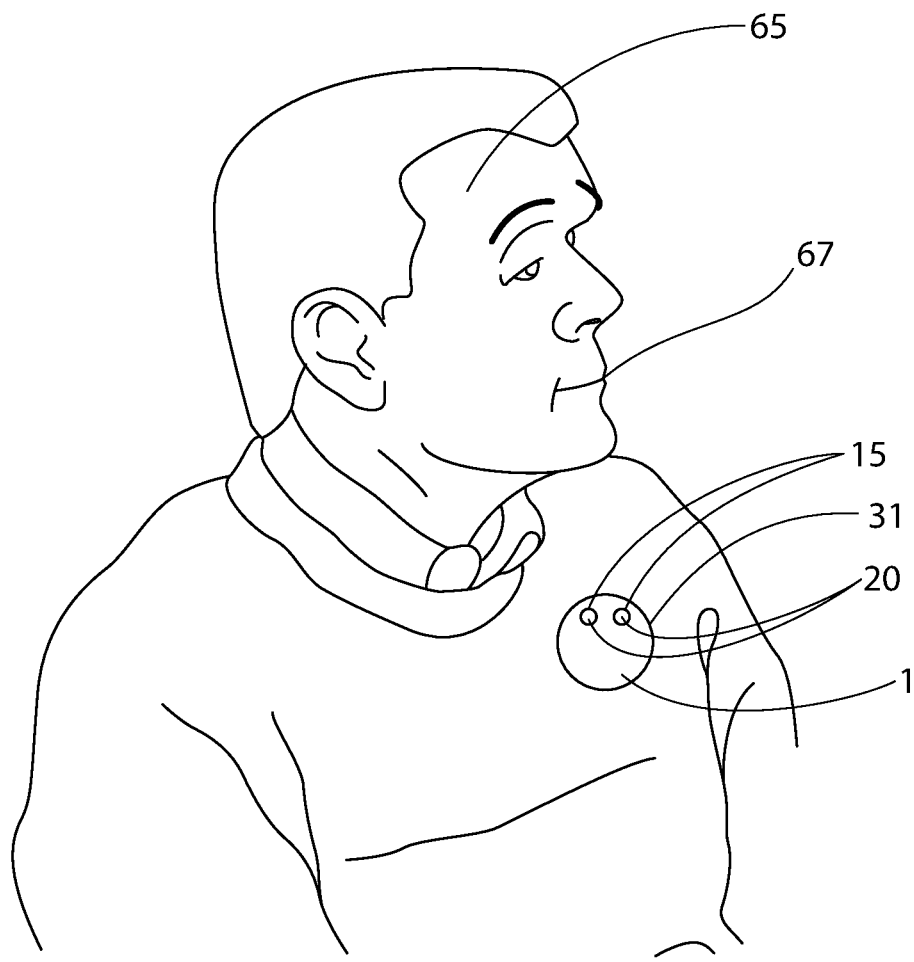
FIG. 1e is a schematic drawing of the device shown in use on a subject.
Figure 1F:
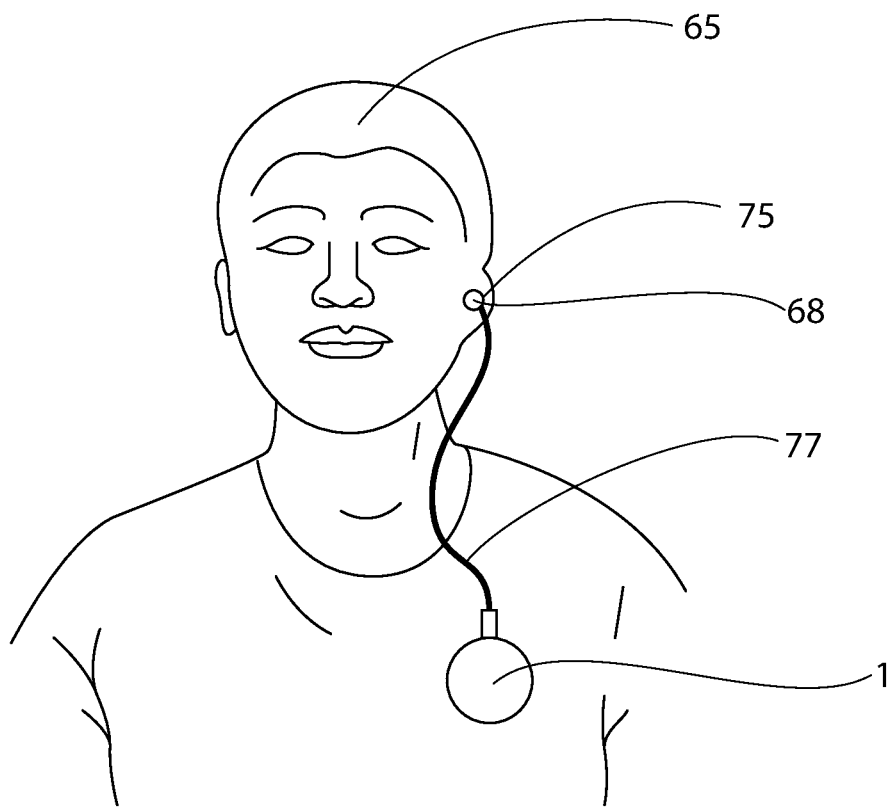
FIG. 1f depicts a non-limiting embodiment of the device in use by a subject having an ear based oximeter attached to the ear lobe of the subject, comprising a lead running from the device to the photosensor.

FIGS. 1a-1d depict schematically one non-limiting embodiment of the device for remote monitoring of food intake and physical activity in a subject. FIGS. 1a, 1b and 1c show top and two side views, respectively of the device 1. As shown in FIGS. 1a-1d, device 1 comprises a housing 5 (cylindrical in this non-limiting embodiment). The housing 5 comprises two holes 15a, 15b through which lenses 20a and 20b of video cameras are exposed. Holes 15a and 15b and lenses 20a and 20b are positioned to record a stereo image. In FIG. 1b, an eating detector 30 is depicted, comprising a light beam projector 31 and a light sensor 32. FIG. 1c depicts a flash memory card slot 45 for receiving a flash memory card, exposed through a hole in the housing 5. FIG. 1d is a cross section of the device 1, showing outer surface 8 and inner cavity 10 of the housing 5 in which electronic components are located. A printed circuit board (PCB) 40 is depicted. The PCB 40 is shown schematically and in reality may comprise any useful electronic structure(s) and configuration. Sensors, data storage, processors, data connectors, e.g., flash memory card slots and USB adaptors, device bus, such as an accelerometer and gyroscope are also located in the inner cavity 10. For example, a data storage device comprising a recorder and a data storage medium, such as a flash memory card, is located within the inner cavity. A microprocessor 48 is located in the inner cavity 10 and is connected to the PCB 40. A battery (not shown) is similarly housed within the interior cavity 10. In one embodiment, a battery is connected to the microprocessor so that the microprocessor manages power consumption of the battery. As shown in FIG. 1a, the device 1 also comprises an aesthetic feature 60, such as the logo of a sports team located on the outer surface 8 of the housing 5. FIG. 1e is a schematic drawing of the device 1 shown in use on a subject 65. The device comprises lenses 20 positioned in the housing 5 to record a stereo image. FIG. 1f depicts a non-limiting embodiment of the device 1 in use by a subject 65 having an ear based oximeter 75 attached to the ear lobe 68 of the subject 65. A lead 77 is shown connecting the device 1 to the oximeter 75. The device 1 is depicted as being worn as a button attached to the shirt of the subject 65.

FIGS. 2a-2c depict schematically a second embodiment of the device 101 for remote monitoring of food intake and physical activity in a subject. The device 101 comprises a housing 105 having a substantially rectangular shape and having an outer surface 108. The two video cameras are positioned to record a stereo image. The lenses 120a, 120b of the video cameras are exposed through holes 115a, 115b in the housing 105. As depicted in FIG. 2b, a card slot 145 is located on the side of the device for receiving a flash memory card. An optical eating detector 130 comprising a light beam projector 131 and a light sensor 132 is located on a side of the device 101 as shown in FIG. 2c. The device 101 also comprises an aesthetic feature 160 such as the logo of a sports team located on the outer surface 108 of the housing 105.

Figure 3:
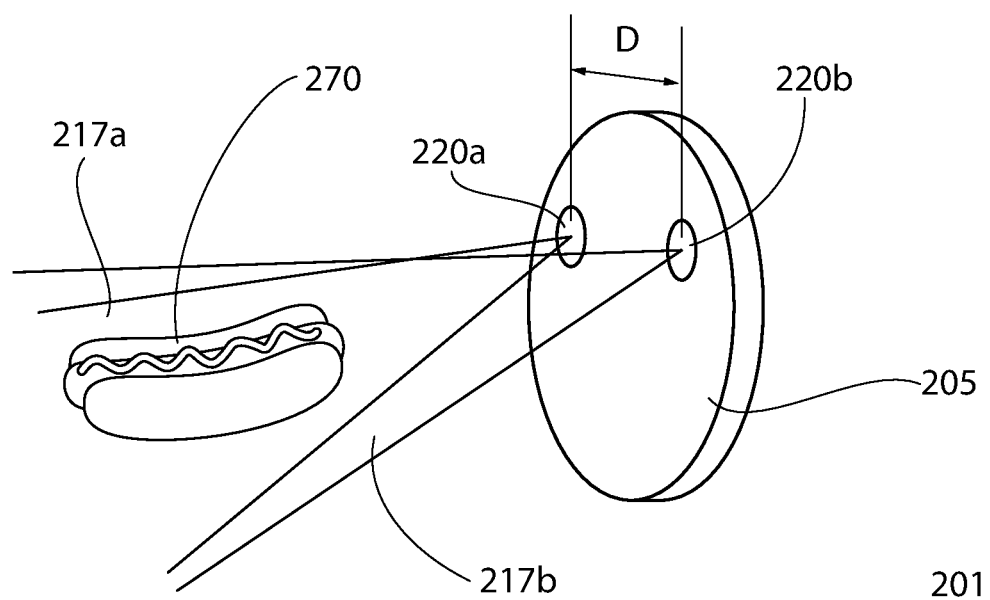
FIG. 3 depicts schematically a non-limiting embodiment of the invention which highlights the placement of the two video cameras.

FIG. 3 depicts schematically a non-limiting embodiment of the device 201 which highlights the placement of lenses 220a and 220b of two video cameras in the housing 205 configured to record a stereo image. The lenses 220a and 220b are separated by a distance D. The field of view 217a and 217b for each video camera is depicted, showing overlap of the respective fields of view on food item 270.

Figure 4:
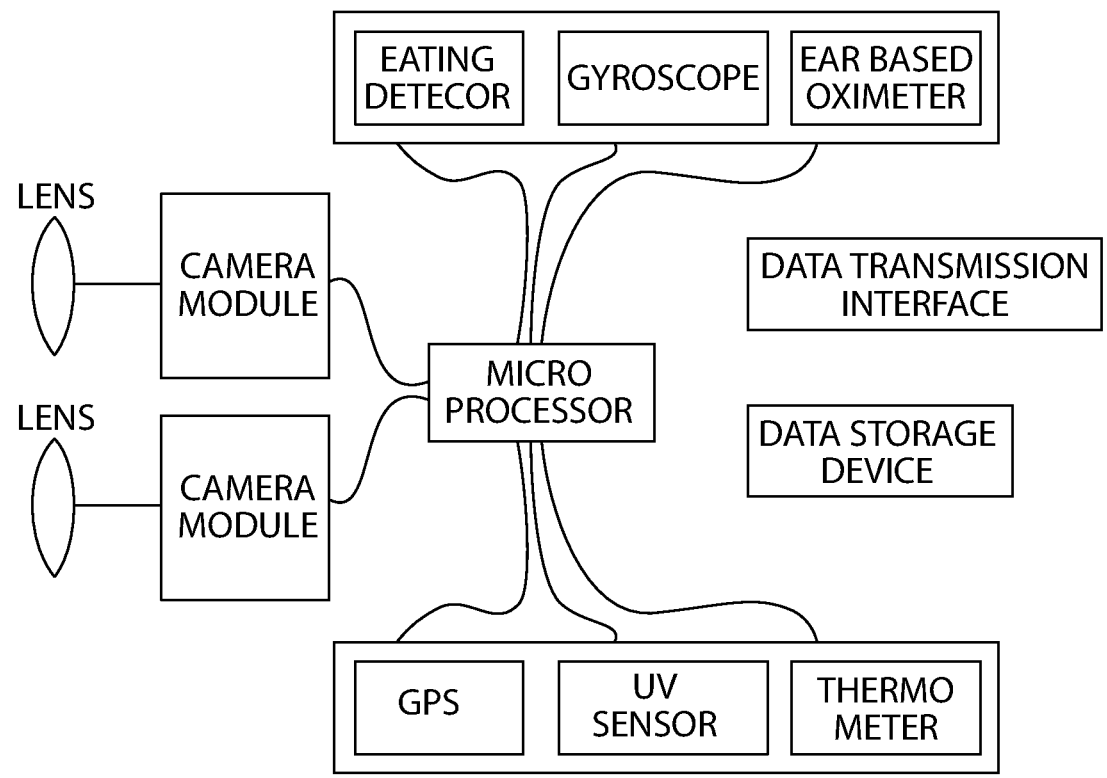
FIG. 4 is a block diagram showing the relationship of electronic components in one non-limiting embodiment of the device.

FIG. 4 is a block diagram showing the relationship of electronic components in one non-limiting embodiment of the device described herein. Lenses from each of two video cameras receive an image and, if optionally equipped with an auto-focus mechanism, focus their lenses for recording by the camera. Similarly, data is collected by physiological sensors, including the accelerometer, gyroscope, eating detector, oxygen saturation sensor, optical sensors, heart rate monitor, and electrode. Signal received from any analog signal source, such as a sensor or camera is converted into digital form by suitably configured analog-to-digital (A/D) converter(s). A microprocessor along with suitable software programs/processes coordinates data acquisition from the camera and the physiological sensors, storage of the data, any required conversion or modification of the data, privacy functions such as data encryption, allocation of system resources for the device as well as any additional processing functions required by the device or system. With suitable software according to certain embodiments of the device, the microprocessor controls the usage of the physiological sensors and the video cameras by turning the devices on and off or, in the case of the video cameras, reducing the frame rate and resolution at times when the sensors and cameras are less likely to record relevant information regarding food consumption and physical activity. The microprocessor is also shown in electronic connection with the data storage device which comprises the recorder and data storage medium. The microprocessor controls and optimizes data storage and ensures efficient use of storage space. The device also comprises a data transmission interface comprising an antenna for sending and receiving data from the device to, e.g., a computer using an acceptable transmission protocol such as Bluetooth. The data transmission interface is designed to be in wireless communication with an external data receiver. The data receiver could be attached to an external source for backing up data such as a hard drive or to a computer for processing data, etc.

Figure 5:
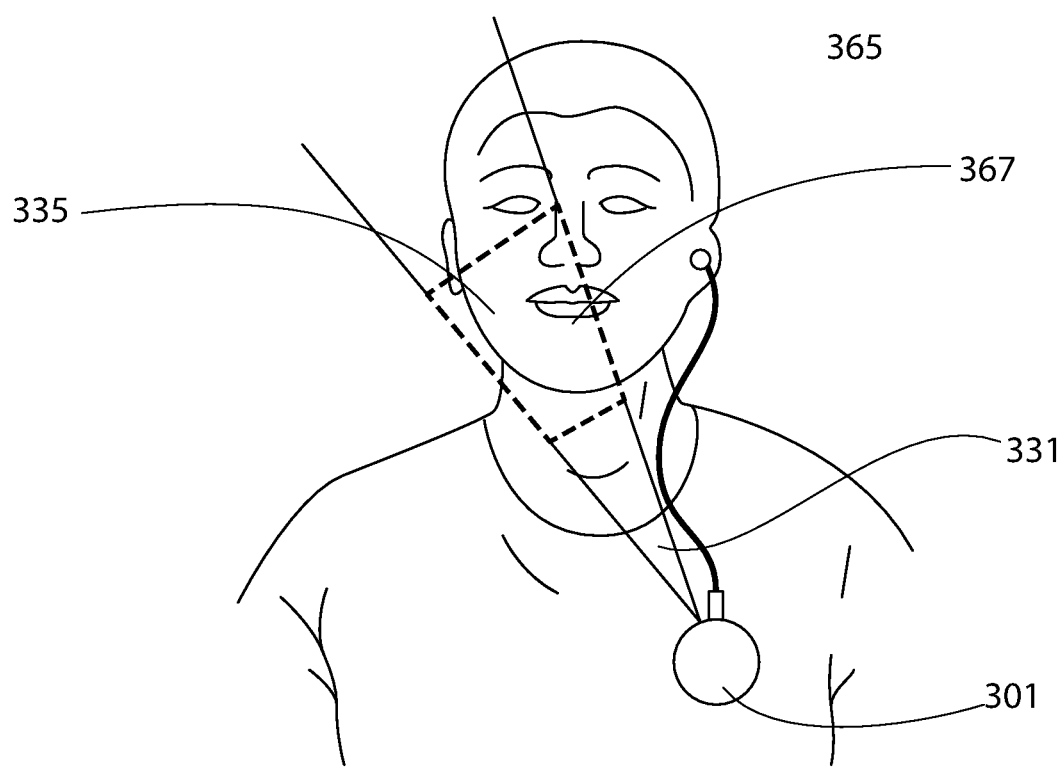
FIG. 5 depicts a schematic drawing showing the optical eating detector in use.

FIG. 5 illustrates an optical eating detector device 301 e.g., the device 1 depicted in FIG. 1a, in use on a subject 365. A beam of light 331 (either infrared or laser) is projected from the device 301. The beam 331 passes in front of the mouth 367 of the subject 365. A light detection zone 335 is defined as the region in front of the mouth 367 of the subject, which is depicted as being trapezoidal in shape in a two-dimensional view. The device 301 includes a light sensor for measuring when an object passes within the detection zone.

Figure 6:
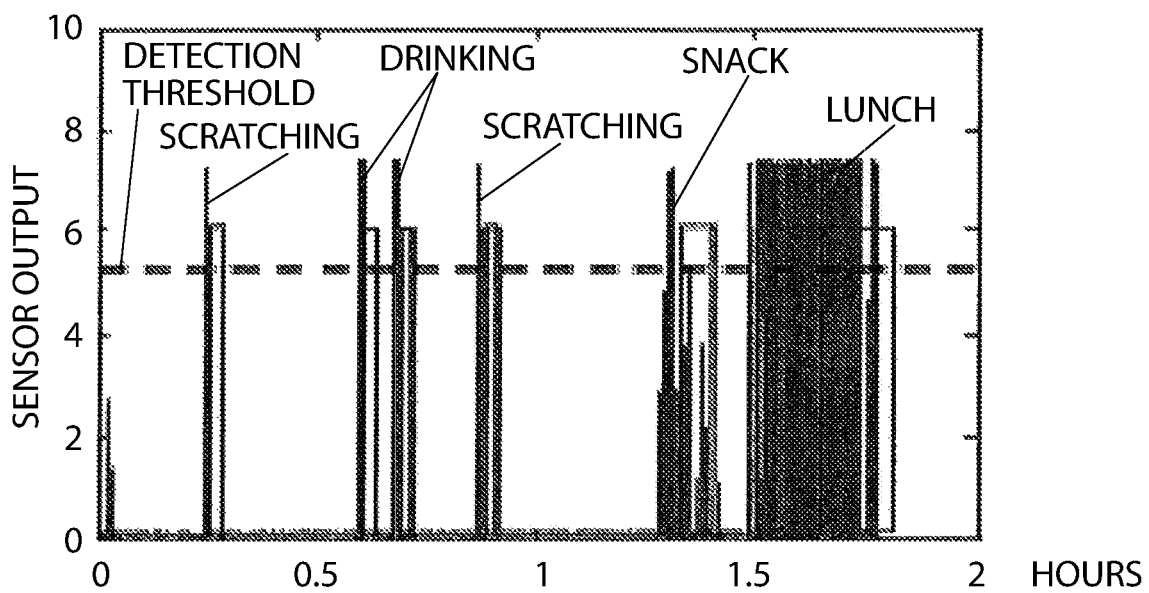
FIG. 6 is a graph displaying data collected from an optical eating detector worn by a subject over a two hour period.

FIG. 6 is a graph showing data obtained from the optical eating detector. The graph presents data recorded while the device is worn by a subject for a two hour period. Each spike indicates activity in the detecting zone. The amplitude of the spike indicates the intensity of the reading by the sensor and corresponds to the volume of the object which passes through the detecting region or, more specifically, to the percentage of the light beam which is obscured. The video camera is set to begin recording when one of the spikes reaches threshold intensity as denoted according to the dashed line. The video camera is set to continue recording for a pre-determined period of time after the sensor is triggered. Any additional triggering activity will re-start timing. The rectangles imposed over the spikes indicate times when the eating detector signals that the video cameras should be recording. The eating detector may also record other events when an object passes in front of the mouth of a subject such as smoking.

Figure 7:
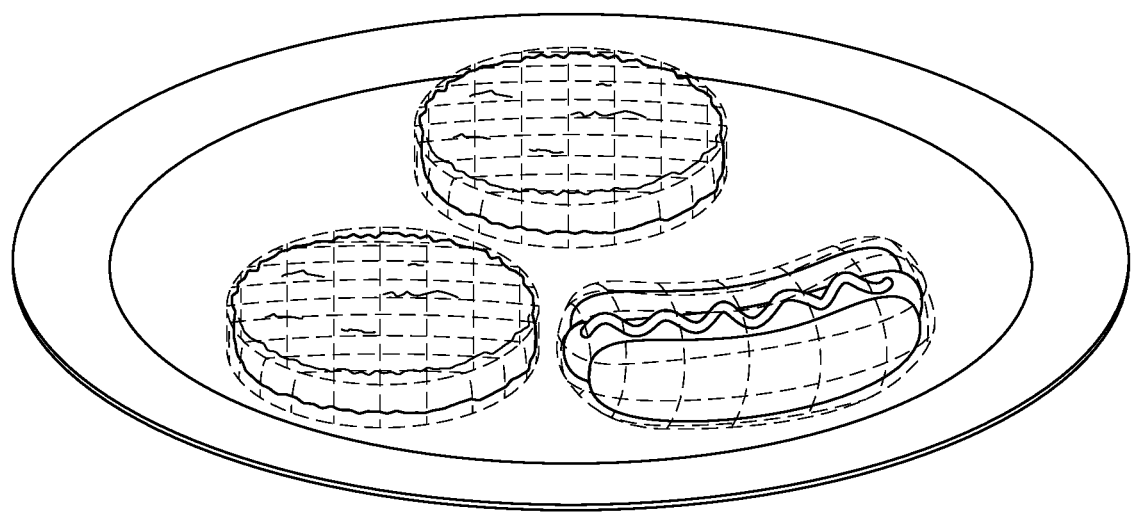
FIG. 7 is a photograph of three food items arranged on a plate. A computer generated template is laid over the food item images to represent how dimensions and volume of the food items are estimated according to one process for estimating food dimensions.

FIG. 7 depicts a computer generated template laid over an image of a food item to demonstrate how the dimensions and volume of the food item are estimated using an automated process using recorded stereo images. While in general, a pair of stereo images can only reconstruct a portion of the 3D food surface, since most food items have roughly known geometries (e.g. a piece of pizza is roughly a triangular prism) it is possible to estimate volume of the entire food item even though the 3D surface of only a small portion of the food item is actually known. Researchers recently developed a virtual reality (VR) method to model food shape from a partial observation. According to the recently developed automated process, a computer-generated template is scaled, rotated, and deformed to virtually fit the food in the image space. In FIG. 7, three food items are arranged on a plate. A computer generated template is oriented to overlay each food item. When the camera is well calibrated, the wireframe virtual template provided an accurate measure of the portion size.

Also provided in the present application is a method of monitoring behavior, condition or activity of a subject. Such parameters may be monitored by recording output of a device comprising a housing; a bus inside the housing; one or more sensors connected to the bus; two or more imaging sensors connected to the bus and positioned in the housing to record a stereo image; an eating detector in the housing and connected to the bus, eating detector comprising a light beam source configured in the device to pass a light beam in front of a subject's mouth when the device is worn by a subject and a light sensor able to measure changes of light intensity in a path of a light beam from the light beam source; a microprocessor connected to the bus; a data storage device connected to the bus and comprising a data storage medium; a program for managing one or more operations of the device including imaging, data acquisition and storage; and a power supply connected to the bus.

For monitoring behavior, in non-limiting embodiments the sensors included in the housing may be any suitable sensors that can collect data sufficient to determine the behavioral patterns of a human or animal. For example, and without limitation, any sensor described herein, such as oximeters, heart rate monitors, accelerometers, and gyroscopes. The sensors may also include environmental sensors like GPS sensors, VOC sensors, magnetometers, electronic or digital compasses, thermometers, humidity sensors, ambient sound recorders, and UV sensors.

In non-limiting embodiments, the method may be used to collect information on behavioral, condition or activity data for specific populations. For example and without limitation, the methods may be used to collect information from police officers, astronauts, or consumers in a shopping environment (e.g. in a particular store or mall). The method may also be used to assess the behavior, condition or activity of animals, for example livestock on a farm or grazing on grazing lands. The livestock may include any domesticated animal including, but not limited, to cattle.

EXAMPLES

The examples described below are examples of validation studies, proposed validation studies or proposed real world uses for the device, system, and method for food intake and physical activity assessment. The examples presented are purely illustrative of potential functionality and uses for various non-limiting embodiments of the device.

Example 1: Determination of Food Dimension Using a Form Fitting Model and Nutritional Content Estimation A preliminary experiment was conducted to validate the stereo vision approach. Two web cameras were placed side-by-side on a support. The intrinsic parameters of the cameras were obtained from the manufacturer and a once-for-all calibration was performed. Stereo pictures of three foods were taken simultaneously. Correspondences of pixels between each stereo image pair were built using a density matching algorithm. Then, real-world 3D coordinates were computed using the aforementioned numerical optimization process. Utilizing the virtual shape models (sphere, cuboid, and cylinder for orange, cheesecake and hamburger, respectively), food volumes were calculated. The average volumetric error for the three cases was 7.3%, a reasonable error for food objects. Preliminary results suggested that the stereo vision approach is feasible in measuring food portion size.

Based on volume estimations described above, calorie and nutrition information could be determined if the food item could be identified. One database that is used for this purpose is the Food and Nutrient Database for Dietary Studies (FNDDS) database. Using the FNDDS, the best match for the recorded food item was determined and calorie and nutrient values were retrieved. Although FNDDS is a vast database (over 13,500 foods), some foods are not listed or absent from volume information. In these cases, under the proposed method, a dietitian studies the composition of the food from various information sources (e.g., recipe and the cultural origin) and provides caloric and nutrient values

Example 2: Physical Activity Assessment: Manual Identification Method

To assess the accuracy of physical activity (PA) identification, an evaluation study with human subjects was conducted. Ten healthy adults wore a prototype device during the daytime. A total of 26 days of data (total about 240 hours) was recorded. The average rate of picture taking was approximately one picture for every two seconds (frame rate 0.5 per sec). In order for the subjects to maintain their normal lifestyle without modifying behavior, they were not told about our physical activity study. Sadly, little intentional physical exercise was performed by these subjects in their normal, but busy daily routines. During data analysis, an automatic algorithm to break the raw image sequences into individual "screenshots" was utlilized. Then, the subjects were asked to watch these screenshots and identify their own PAs. The results were then saved as gold standards. Next, all of the labeled screenshots from the different human subjects were randomized and incorporated into a single pool of data. Finally, images from the randomized data pool were shown to a new group of participants to access the accuracy of identifying the physical activity being performed. Each time, a screenshot was randomly drawn from the pool for the observer to identify the event. His/her entry was then compared against the gold standard. Despite the complexity of the daily-life activities, there were on average of 85.7% cases where the observers' results agreed with the gold standard. Although these results have not been compared with conventional methods (e.g., using accelerometers), it would be difficult for these methods to achieve a comparable accuracy with respect to these complex real-life activities.

Example 3: Physical Activity Assessment Automated Method

An automated process has been proposed whereby a computer analyzes video data according to a categorization algorithm to identify physical activities performed by the subject. Under the proposed approach, the set of potential physical activities is decomposed into a set of Eigen activities (EAs), which can be more easily classified by a computer. The EA concept is parallel to a powerful mathematical concept where a large number of functions can be approximated using a much smaller set of basic functions. Briefly, the data is first filtered and broken down using an improved segmentation algorithm. Then, the measured PA data within each "screenshot" is pre-processed individually to extract "features". Next, a classifier will be used to classify the feature vectors into Eigen activities (EAs). This EA sequence will be analyzed by the second classifier that determines physical activities based on a hidden Markov model or a linguistic model. Methods and preliminary data are described in more detail below.

Recently [L. Li, H. Zhang, W. Jia Z.-H. Mao, and M. Sun, "Indirect Activity Recognition Using a Target-Mounted Camera," Proc. IEEE 4th Int. Conf. Image and Signal Processing (CISP'11), Shanghai, China, 2011.], we reported an automatic method for identifying six basic EAs (walking, bowing, crouching, waist turning, sitting-still, sitting-up) by processing video data was reported. Since the wearer of the device never appears in the video, EAs were recognized indirectly by examining the motion vectors in the image sequence. Recognition involved three steps: (1) identifying pixel correspondences that produced motion vectors between adjacent images; (2) building pattern features from the histograms of the motion vectors in each pair of images; (3) recognizing the PA using a classifier. Classifiers tested were the K-Nearest Neighbor (KNN), Naive Bayesian and Support Vector Machine (SVM) classifiers. Results showed that the classification accuracy depended on the quantization levels of motion vector directions. The SVM was the most accurate classifier in our test (95%), while the KNN was the least accurate one (85%). In another work, five different EAs were recognized to recognize PAs expressed as the combinations of these activities.

Future study seeks to identify PA when the video recording frame rate varies considerably. Therefore, the motion vector may become ambiguous when the frame rate decreases. However, certain of the devices described herein for monitoring food intake and physical activity are constructed to provide multiple forms of sensor data including accelerometer, gyroscope, GPS, oximeter, and UV sensor data. Data is collected from these multiple sensors and used, in combination with the video data, to identify the physical activity performed. Data from multiple sensors is processed either utilizing normalized features directly to determine EAs or to implement a dimension reduction algorithm, such as the one based on the principal component analysis (PCA). The performances of the two cases are compared experimentally. During the research, sets of EAs are chosen according to the following criteria: 1) they are suitable to the data produced by our sensors; 2) they are as independent as possible—in parallel to the concept of using a basis in mathematics—thus their combinations can represent a larger set of physical and sedentary activities; and 3) the number of EAs is reasonably small to facilitate data processing. The relationships between feature patterns and EAs will be established using a well-established forward algorithm.

Once the set of EAs is chosen, it is applied for the recognition of physical activity in video data. In a preliminary experiment, the class of "indoor activities" was represented as a temporal sequence of events (represented by feature patterns) in an ordered form H1, H2, . . . , HT. Using the temporal sequence, a hidden Markov model (HMM) with parameters Θm was obtained from the aforementioned forward algorithm. Given k classes of activities, the observed data was classified by the following optimization process: where P(H1, H2, . . . , HT|Θm) is the HMM density function and c is the determined class. Experimentally, five types of common indoor activities were reviewed from field-acquired real-world videos acquired by the wearable camera.

In addition to the uses described above (namely as a way to obtain objective data about diet and exercise as part of a treatment for diabetes, obesity, or during athletic training), alternate embodiments of the invention are useful for additional purposes.

Example 4: Police Protection

A device as described herein is expected to be useful to police departments for automatically documenting important events by individual officers. According to one embodiment, the device comprises two cameras with either auto-focusing capability or a focus range between, e.g., two and twenty feet. The device also optionally comprises accelerometer, gyroscope, and GPS sensors. Notably, the GPS function could be used to track the location of officers throughout the day. Face-recognition software can be included to focus on individuals surrounding the officer. The software optionally triggers high-resolution imaging when a face comes into the view of the cameras. The device also optionally comprises a "panic button" to indicate that the officer needs assistance. Data, such as GPS location information and images are optionally transmitted by a wireless transmitter in the device, such as WiFi or Bluetooth and/or over cellular or other networks to a central location such as a police station so that the location of each officer is known in real time and, optionally, images and sound in the field when transmission of these data are necessary. The physiological sensors could also track what sorts of physical activities each officer performs on a daily basis, to better understand how often officers must run, sprint, or walk during the performance of their duties. In some cases, physical data, such as that an officer is running for an extended period could be a sign that the officer is chasing a perpetrator and is in need of back up. Computer monitoring of these variables may trigger automatic acquisition of field images and alert personnel in the central data collection facility. The central facility could automatically send additional officers.

Example 5: Astronaut Exploration

A device as described herein is expected to be useful to monitor daily activities of an astronaut during a space mission. Information about the eating habits, daily physical exertion, and environmental factors such as radiation exposure could be used to ensure that astronauts remain in good health throughout the mission. As stated in previous sections, individuals who must keep track of the information by themselves typically under report the calories consumed each day and over report physical activity. The device of the present invention would provide more accurate data regarding astronaut calorie consumption to better modify astronaut diets in light of the physical demands of the job. Because food typically is packaged in single-meal containers, barcodes or similar 2D indicators, such as QR codes (e.g. JAGTAGs), can be used to identify food items.

Example 6: Consumer Expectations and Habits Data

The device also monitors shopping habits of consumers such as consumers in a supermarket. For example, a supermarket could enlist a number of shoppers to wear the device while shopping at the store. The GPS sensor tracks the shopper's location to better understand the path the shopper uses while navigating through the store. In addition, the physiological sensors could be used to determine how fast the shopper is moving in each area of the store. The store may use this data to determine which advertising efforts are effective (i.e. causing the shopper to slow down and more closely examine the products) and which efforts are less successfully (the shopper quickly walks through the area without examining the merchandise). Similarly, the video cameras could be used to determine which products the shopper looks at and for how long. The device may be used to study the shopping process involving interactions between two or more people. For example, it may monitor how a shopper's decision is influenced by his/her spouse or children. In addition, the video camera or another sensor on the device, such as a bar code scanner, could be used to keep track of which products the shopper picks up, examines, or places in his or her cart. This data regarding the consumers interaction with specific goods could be used to more quickly restock shelves or, potentially, to shorten the checkout process by keeping a real time record of which goods are currently in the shopper's cart. Physiological sensors such as the heart rate monitor would provide additional data concerning the consumer's response to various products and advertising techniques. This data regarding the way shoppers move around the store and how shoppers respond to different advertising techniques could be used to improve the physical layout of stores and to present products to consumers in effective ways.

Example 7: Data Collection for Animals

A device as described herein is expected to be useful for measuring physiological health, eating habits, and location of animals in the wild. In one example, the device is attached to an animal for a period of months or years. The data provided, concerning physical health, eating activities, and location, could help to better understand the impact of changes to the environment such as deforestation or climate change on the physiological health of individual species. For this embodiment, the device could be equipped with a data storage recorder capable of recording data for several weeks at a time. Researchers could locate the animal and recover a removable disk from the device as necessary or download data via wireless communication. The device could also be equipped with a long range wireless transmitter to continuously transmit data to a research facility.

A device as described herein can be used to monitor farm animals. For example, by affixing a device to the head of a cow, the activities, such as eating, resting, drinking, moving, and interacting with other animals, can be monitored for a long period of time without disturbing the animal. When both the calorie/nutrient intake and calorie expenditure of the cow are known, cattle raising methods can be optimized accordingly to maximize the production of milk with high quality.

Whereas particular embodiments of this invention have been described above for purposes of illustration, it will be evident to those skilled in the art that numerous variations of the details of the present invention may be made without departing from the invention as defined in the appended claims.

We claim:

1. A device configured to be worn on a subject for remote monitoring of food intake and physical activity in a subject, comprising:
    a wearable housing;
    a bus inside the housing;
    a physical activity or physiological sensor connected to the bus;
    two or more imaging sensors connected to the bus and positioned in the housing to record a stereo image;
    an eating detector in the housing and connected to the bus, the eating detector comprising a light beam source configured in the device to pass a light beam in a path in front of the subject's mouth and a light sensor configured to measure light intensity data representative of a presence or absence of an object in the path of the light beam;
    a microprocessor connected to the bus;
    a data storage device connected to the bus and comprising a data storage medium;
    programming instructions, stored on the data storage device, that when executed by the microprocessor cause the microprocessor to:
        receive the light intensity data from the light sensor;
        identify based on a comparison between the received light intensity data and light intensity when objects are absent from the path of the light beam that the object is in the path of the light beam and thus determine when the subject is eating;
        generate a signal to control the imaging sensors to obtain images of the object in the path of the light beam based on the determination that the object is in the path of the light beam; and
        generate, from the images a stereo image of the object in the path of the light beam; and
    a power supply connected to the bus.

2. The device of claim 1, in which data stored on the data storage device is encrypted.

3. The device of claim 1, in which the data storage device comprises a removable flash memory card.

4. The device of claim 1, in which the device further comprises a data transmission interface connected to the bus.

5. The device of claim 4, further comprising programming instructions, stored on the data storage device, that when executed by the microprocessor cause the microprocessor to receive data from an external computer representative of physical activity and/or a physiological condition of the subject and to compare the received data with data for the physical activity and/or physiological condition of the subject obtained from the physical activity sensor or physiological sensor of the device.

6. The device of claim 4, in which the data transmission interface operates under WiFi, cellular network or Bluetooth protocols.

7. The device of claim 4, in which the data transmission interface comprises a wired data communications interface.

8. The device of claim 1, wherein the physical activity sensor comprises one or more of an accelerometer, a gyroscope, an ultraviolet sensor, a magnetometer, or an audio sensor, or wherein the physiological sensor comprises an oximeter.

9. The device of claim 1, wherein the imaging sensors comprise cameras, and wherein output from the light sensor of the eating detector controls recording from the cameras by either modifying a frame rate of the cameras or turning the cameras off or on.

10. The device of claim 1, in which the light beam source of the eating detector is a laser.

11. A method of monitoring behavior, condition or activity of a subject with the remote monitoring device of claim 1, the method comprising:
    a) recording, with a computer comprising a processor and a data storage device, output of the remote monitoring device affixed to the subject on the data storage device of the computer; and
    b) processing, with the processor of the computer, the output of the remote monitoring device affixed to the subject to produce information relating to a behavior or activity of the subject.

12. The method of claim 11, comprising:
    a) recording image data from the two or more imaging sensors suitably positioned on the subject to record a stereo image pair of food consumed by the subject and an image of the physical activity of the subject; and
    b) determining from the image data one or both of food consumption by the subject and physical activity of the subject.

13. The method of claim 11, in which the remote monitoring device comprises two cameras, an accelerometer, a gyroscope, a heart rate monitor, an oximeter, and a global positioning system (GPS) sensor, wherein the subject is a police officer and the data recorded includes environmental data and physiological data.

14. The method of claim 11, in which the remote monitoring device comprises a GPS sensor, a heart rate monitor, and an accelerometer, and in which the subject is a consumer in a shopping environment and the data recorded includes geographical and physiological data.

15. The method of claim 11, in which the device comprises two cameras, a GPS sensor, a heart rate monitor, an accelerometer, and an oximeter, wherein the subject is livestock and the data recorded includes geographical and physiological data.

16. The method of claim 11, in which the device comprises two cameras, an accelerometer, a gyroscope, a GPS sensor, an oximeter, and a UV sensor.

17. The device of claim 1, in which a fitting algorithm for determining dimensions of a food item causes the microprocessor to generate a representation of the stereo image of the food item in a three dimensional perspective, scale and orient a virtual template shape to fit the food item depicted in the stereo image representation and estimates a volume of the food item by determining the volume of the virtual template shape.

18. The device of claim 1, further comprising a global positioning sensor and the system comprises a database comprising environmental quality information for different locations and a computer program for estimating effects of environmental quality for a physiological condition of the subject based on location data obtained from the global positioning sensor, weather data obtained from environmental monitoring sensors on the remote monitoring device, and the database comprising environmental quality information.

19. The device of claim 1, wherein the programming instructions further cause the microprocessor to: determine a dimension of the food item based on the stereo image of the food item, a distance between the two or more imaging sensors, and a fitting algorithm which fits a virtual template shape to the stereo image of the food item.

20. The device of claim 1, wherein the housing comprises a front surface, a rear surface, and a side surface extending between the front surface and the rear surface, and wherein a field of view of the one, two, or more imaging sensors passes through at least one opening on the front surface of the housing to capture images of items in front of the subject, and wherein the light beam source directs the light beam through an opening on the side of the housing, such that the light beam passes in front of the subject's mouth.

* * * * *